US009765169B2

(12) United States Patent
Das et al.

(10) Patent No.: US 9,765,169 B2
(45) Date of Patent: Sep. 19, 2017

(54) FUNCTIONALIZED POLYMER HYBRIDS

(71) Applicant: CARNEGIE MELLON UNIVERSITY, Pittsburgh, PA (US)

(72) Inventors: Subha Ranjan Das, Pittsburgh, PA (US); Saadyah Averick, Pittsburgh, PA (US); Sourav K. Dey, Pittsburgh, PA (US); Krzysztof Matyjaszewski, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 147 days.

(21) Appl. No.: 14/785,334

(22) PCT Filed: Apr. 17, 2014

(86) PCT No.: PCT/US2014/034532
§ 371 (c)(1),
(2) Date: Oct. 17, 2015

(87) PCT Pub. No.: WO2014/172557
PCT Pub. Date: Oct. 23, 2014

(65) Prior Publication Data
US 2016/0075810 A1 Mar. 17, 2016
US 2017/0152336 A9 Jun. 1, 2017

Related U.S. Application Data

(60) Provisional application No. 61/854,143, filed on Apr. 18, 2013, provisional application No. 61/965,397, filed on Jan. 29, 2014.

(51) Int. Cl.
C12Q 1/68 (2006.01)
C08F 251/00 (2006.01)
C07H 21/00 (2006.01)
C07H 1/00 (2006.01)

(52) U.S. Cl.
CPC ............. C08F 251/00 (2013.01); C07H 1/00 (2013.01); C07H 21/00 (2013.01)

(58) Field of Classification Search
CPC .......... C07H 1/00; C07H 21/00; C08F 251/00
USPC ....................................................... 526/268
See application file for complete search history.

(56) References Cited

U.S. PATENT DOCUMENTS

| | | |
|---|---|---|
| 5,262,530 A | 11/1993 | Andrus |
| 5,763,548 A | 6/1998 | Matyjaszewski |
| 5,789,487 A | 8/1998 | Matyjaszewski |
| 5,807,937 A | 9/1998 | Matyjaszewski |
| 5,945,491 A | 8/1999 | Matyjaszewski |
| 6,111,022 A | 8/2000 | Matyjaszewski |
| 6,114,518 A | 9/2000 | Pitner |
| 6,121,371 A | 9/2000 | Matyjaszewski |
| 6,124,411 A | 9/2000 | Matyjaszewski |
| 6,162,882 A | 12/2000 | Matyjaszewski |
| 6,407,187 B1 | 6/2002 | Matyjaszewski |
| 6,512,060 B1 | 1/2003 | Matyjaszewski |
| 6,538,091 B1 | 3/2003 | Matyjaszewski |
| 6,541,580 B1 | 4/2003 | Matyjaszewski |
| 6,624,262 B2 | 9/2003 | Matyjaszewski |
| 6,627,314 B2 | 9/2003 | Pyun et al. |
| 6,759,491 B2 | 7/2004 | Matyjaszewski |
| 6,790,919 B2 | 9/2004 | Matyjaszewski |
| 6,887,962 B2 | 5/2005 | Matyjaszewski |
| 6,994,964 B1* | 2/2006 | Chang ............... C07H 21/00 435/6.11 |
| 7,019,082 B2 | 3/2006 | Matyjaszewski |
| 7,049,373 B2 | 5/2006 | Matyjaszewski |
| 7,064,166 B2 | 6/2006 | Matyjaszewski |
| 7,125,938 B2 | 10/2006 | Matyjaszewski |
| 7,157,530 B2 | 1/2007 | Matyjaszewski |
| 7,332,550 B2 | 2/2008 | Matyjaszewski |
| 7,407,995 B2 | 8/2008 | Ok |
| 7,572,874 B2 | 8/2009 | Matyjaszewski |
| 7,678,869 B2 | 3/2010 | Matyjaszewski |
| 7,795,355 B2 | 9/2010 | Matyjaszewski |
| 7,825,199 B1 | 11/2010 | Matyjaszewski |

(Continued)

FOREIGN PATENT DOCUMENTS

| | | |
|---|---|---|
| WO | WO2004087777 | 10/2004 |
| WO | WO2005087818 | 9/2005 |

(Continued)

OTHER PUBLICATIONS

Averick, Saadyah et al., Direct DNA Conjugation to Star Polymers for Controlled Reversible Assemblies, Bioconjugate Chemistry, 2011, vol. 22, No. 10, pp. 2030-2037.
Jakubowski, Wojciech et al., Activators Regenerated by Electron Transfer for Atom-Transfer Radical Polymerization of (Meth)acrylates and Related Block Copolymers, Angewandte Chemie, 2006, vol. 118, No. 27, pp. 4594-4598.
Averick, Saadyah et al., Solid-Phase Incorporation of an ATRP Initiator for Polymer—DNA Biohybrids, Angewandte Chemie, International. Edition. 2014, vol. 53, No. 10, pp. 2739-2744.
Lou, Xinhui, et al., Detection of DNA Point Mutation by Atom Transfer Radical Polymerization, Anal. Chem. 2005, 77, 4698-4705.

(Continued)

Primary Examiner — Ling Choi
Assistant Examiner — Chun-Cheng Wang
(74) Attorney, Agent, or Firm — Bartony & Associates. LLC.

(57) ABSTRACT

A method of synthesizing a polynucleotide composition includes attaching a compound including at least one initiator or at least one transfer agent for a reversible deactivation radical polymerization to an end of a nucleotide chain assembly immobilized upon a solid phase support during a solid phase synthesis of a polynucleotide so that the initiator or the transfer agent is attacked to the end of a nucleotide chain assembly in a manner which is stable under conditions of deprotection of the polynucleotide, and growing a polymer from the initiator of from a site of the chain transfer agent via the reversible deactivation radical polymerization to form the polynucleotide composition.

23 Claims, 9 Drawing Sheets

(56) References Cited

U.S. PATENT DOCUMENTS

| | | | |
|---|---|---|---|
| 7,893,173 | B2 | 2/2011 | Matyjaszewski |
| 7,893,174 | B2 | 2/2011 | Matyjaszewski |
| 8,252,880 | B2 | 8/2012 | Matyjaszewski |
| 8,273,823 | B2 | 9/2012 | Matyjaszewski |
| 8,349,410 | B2 | 1/2013 | Huang |
| 8,367,051 | B2 | 2/2013 | Matyjaszewski |
| 8,404,788 | B2 | 3/2013 | Matyjaszewski |
| 8,445,610 | B2 | 5/2013 | Kwak |
| 2004/0204556 | A1 | 10/2004 | Matyjaszewski |
| 2011/0060107 | A1 | 3/2011 | Matyjaszewski |
| 2011/0065875 | A1 | 3/2011 | Matyjaszewski |

FOREIGN PATENT DOCUMENTS

| | | |
|---|---|---|
| WO | WO2007025086 | 3/2007 |
| WO | WO2007078819 | 7/2007 |
| WO | WO2007075817 | 10/2007 |
| WO | WO2008148000 | 12/2008 |
| WO | WO2009111725 | 9/2009 |
| WO | WO2010111708 | 9/2010 |
| WO | WO2012091965 | 7/2012 |
| WO | WO2013028756 A1 | 2/2013 |
| WO | WO2014172557 | 10/2014 |

OTHER PUBLICATIONS

Lou, Xinhui, et al., Core-Shell Au Nanoparticle Formation with DNA-Polymer Hybrid Coatings Using Aqueous ATRP, Biomacromolecules, 2007, 8, 1385-1390.

He, Peng et al., Synthesis of Surface-Anchored DNA-Polymer Bioconjugates Using Reversible Addition-Fragmentation Chain Transfer Polymerization, Biomacromolecules, 2009, 10, 1804-1809.

Mei, Ying et al., Solid-Phase ATRP Synthesis of Peptide-Polymer Hybrids, J. Am. Chem. Soc. 2004, 126, 3472-3476.

Lou, Xinhui, et al., DNA-Accelerated Atom Transfer Radical Polymerization on a Gold Surface, Langmuir 2006, 22, 2640-2646.

Matyjaszewski, K., et al., Fundamentals of Atom Transfer Radical Polymerization, Eds. Handbook of Radical Polymerization; Wiley: Hoboken, 2002 chapter 11 pp. 523-628.

Matyjaszewski, K.; Xia, J.; Atom Transfer Radical Polymerization; Chem. Rev. 2001, 101, 2921-2990.

Braunecker, W. A.; et al.; Controlled/Living Radical Polymerization: Features, Developments, and Perspectived; Progress in Polymer Science 2007, 32, 93-146.

Siegwart, D. J.; et al.; ATRP in the Design of Functional Materials for Biomedical Applications; Prog. Polym. Sci. 2012, 37, 18-37.

Hawker, C. J.; et al.; New Polymer Synthesis by Nitroxide Mediated Living Radical Polymerizations; Chemical Reviews 2001, 101, 3661-3688.

Moad, G.; et al.; Living Radical Polymerization by the RAFT Process—A Third Update, Aust. J. Chem. 2012, 65, 985-1076.

Tasdelen, M.A. et al., Telechelic Polymers by Living and Controlled/Living Polymerization Methods, Prog. Polym. Sci. 2011, 36, 455-567.

Averick, et al.; ATRP under Biologically Relevant Conditions: Grafting from a Protein; ACS Macro Lett. 2012, 1, 6-10.

Tsarevsky, Nicolay V. et al.; Deactivation Efficiency and Degree of Control over Polymerization in ATRP in Protic Solvents; Macromolecules, 2004, 37 (26), pp. 9768-9778.

Nicolas, J. et al., Nitroxide-mediated Polymerization, Progress in Polymer Sci., 2013, 38, 63-235.

Konkolewicz, D., et al., Visible Light and Sunlight Photoinduced ATRP with ppm of Cu Catalyst, ACS Macro Lett. 2012, 1, 1219-1223.

Simakova, A., et al.; Aqueous ARGET ATRP; Macromolecules, 2012, 45(16): 6371-6379.

* cited by examiner

FUNCTIONALIZED POLYMER HYBRIDS

CROSS-REFERENCE TO RELATED APPLICATIONS

This application is a US National Phase of the International PCT patent application number: PCT/US2014/034532 filed on Apr. 17, 2014, which claims benefit of U.S. Provisional Patent Application Ser. No. 61/854,143, filed Apr. 18, 2013 and U.S. Provisional Patent Application Ser. No. 61/965,397 filed Jan. 29, 2014, the disclosures of which are incorporated herein by reference.

GOVERNMENTAL INTEREST

This invention was made with government support under grant no. DMR 09-69301 awarded by the National Science Foundation and grant no. DMR W81XWH1120073 awarded by the Department of Defense. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Functional biomaterials can be used to solve some of the most vexing diagnostic and drug-delivery challenges. One of the major classes of biomaterials designed to resolve such limitations in treatment is based on functionalized polynucleotides such as nucleic acids; including both deoxyribonucleic acids (DNA) and ribonucleic acids (RNA). Nucleic acid-polymer hybrids (NAPH), including, but not limited to, DNA and RNA-polymer hybrids, DNAPH and RNAPH respectively, are an important segment of this field, and well defined NAPH can be used for several emerging biomedical applications including responsive polymer assemblies, non-covalent linkers for protein-polymer hybrids, DNA adjuvants, sensors and drug delivery vehicles.

In a number of studies, reversible deactivation radical polymerization (RDRP) methods have been utilized for the preparation of bio-conjugates. In general, RDRP procedures exhibit tolerance towards functional monomers and functional groups present in nucleic acids and drugs. The three most common RDRP methods are atom transfer radical polymerization (ATRP), nitroxide mediated polymerization (NMP) and reversible addition fragmentation transfer (RAFT) systems, each of which allow unprecedented control over polymer properties such as dimensions (molecular weight), uniformity (polydispersity), topology (geometry), composition and functionality.

There are two methods to conjugate polymers to DNA. In "grafting-to" methods, the DNA and a preformed polymer are conjugated using high yield linking chemistries, frequently called "click" chemistry. In "grafting-from" methods, an initiator or transfer agent is immobilized onto DNA and a copolymer is formed through an in situ chain extension polymerization reaction. Technically, polymers conjugated to DNA in this method are graft copolymers but the method has also been referred to as "blocking-from".

An advantage of "grafting-to" procedures is that the precise composition of the DNA and each polymer segment are known before conjugation. Currently the majority of DNA-polymer conjugates, wherein the polymers are prepared using RDRP, have utilized a grafting-to procedure using "click" chemistries. Even using high-yield "click" chemistry, however, significant effort must be expended for purification to remove unreacted reactants.

There have been a few studies of a "grafting from" or "blocking-from" strategy for making DNA block copolymers using either ATRP or reversible addition-fragmentation chain transfer (RAFT) polymerization. In those studies, the DNA was functionalized with an amine that could be reacted in solution with an activated ester on a molecule including the initiator or transfer agent functionality. The DNA with the randomly incorporated functionality was subsequently immobilized on gold surfaces or gold nanoparticles. After immobilization, the polymer was grown from the randomly incorporated functionality. As the polymers were grown from surfaces via the attached DNA, any direct analysis and characterization of the DNA block copolymers was precluded.

ATRP has also been used for "grafting-from" or "blocking-from" accessible amine groups on proteins that were modified by reaction with low molecular weight molecules including ATRP initiator functionality. The functionalization procedure was neither site specific nor quantitative.

SUMMARY

In one aspect, a method of synthesizing a polynucleotide composition includes attaching a compound including at least one initiator or at least one transfer agent for a reversible deactivation radical polymerization to an end of a nucleotide chain assembly immobilized upon a solid phase support during a solid phase synthesis of a polynucleotide so that the initiator or the transfer agent is attached to the end of a nucleotide chain assembly in a manner which is stable under conditions of deprotection of the polynucleotide, and growing a polymer from the initiator or from a site of the chain transfer agent via the reversible deactivation radical polymerization to form the polynucleotide composition. In a number of embodiments, the initiator or the chain transfer agent is attached to the end of a nucleotide chain assembly in a manner which is stable under conditions of detachment of the polynucleotide from the solid phase support. The polymer may, for example, be grown from the polynucleotide while the polynucleotide is attached to the solid phase support or after the polynucleotide is detached from the solid phase support. The polynucleotide may, for example, be a ribonucleic acid (RNA), a deoxyribonucleic acid (DNA), a DNA/RNA hybrid, or a derivative or analog thereof. The compound may be attached to the polynucleotide (that is, to the completed nucleotide chain assembly) at an intermediate position within polynucleotide or at the terminus of the polynucleotide.

In a number of embodiments, the compound including the initiator or the transfer agent has the formula $R^1$-L-$(R^2—)_n—R^3$, wherein $R^1$ includes a group adapted to react with the end of the nucleotide chain assembly, L is a base stable spacer group, wherein $R^2$ is a base stable linking group, wherein n is 0 or an integer in the range of 1 to 20, and $R^3$ is a residue of an initiator or a residue of a chain transfer agent for a reversible deactivation radical polymerization (that is, a group including a functional atom or group selected to participate in a reversible deactivation radical polymerization). L may, for example, be selected from the group consisting of

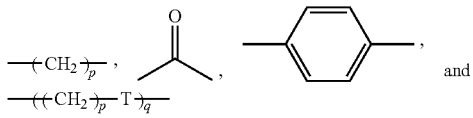

wherein T is selected from the group O, S, —C(O)NH— or —NHC(O)—, p is an integer between 1 and 18 and q is an integer between 1 and 18. In a number of embodiments, $R^2$ is selected from the group consisting of

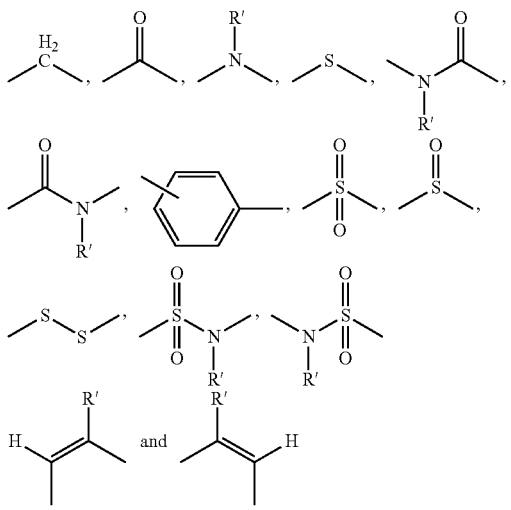

wherein R' is selected from the group of H, alkyl and aryl.

$R^1$ may, for example, include or be a phosphoramidite group, an azide group, an alkyne group, an N-hydroxysuccinimide ester group, a maleimide group, a dibromomaleimide group or a thiol group. In a number of embodiments, $R^1$ is a phosphoramidite group. In a number of embodiment, the phosphoramidite group ($R^1$) has the formula

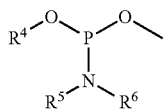

wherein $R^4$ is $(CH_2)_rCN$, wherein r is an integer in the range of 1 to 5, and $R^5$ and $R^6$ are each independently selected from the group consisting of methyl, ethyl, propyl, pentyl, hexyl or heptyl. $R^4$ may, for example, be a 2-cyanoethyl group. In a number of embodiments, $R^5$ and $R^6$ are each isopropyl.

In a number of embodiments, $R^3$ has the formula:

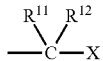

wherein X is a homolytically cleavable (atom or) group or a group activated by degenerative radical exchange;

$R^{11}$ and $R^{12}$ are each independently selected from the group consisting of a homolytically cleavable group, a group activated by degenerative radical exchange, H, $C_1$-$C_{20}$ alkyl (in a number of embodiments, $C_1$-$C_{10}$ alkyl or $C_1$-$C_6$ alkyl), $C_3$-$C_8$ cycloalkyl, C(=Y)$R^{15}$, C(=Y)N$R^{16}R^{17}$, COCl, OH (in a number of embodiments, only one of $R^{11}$ and $R^{12}$ is OH), CN, $C_2$-$C_{20}$ alkenyl or alkynyl (in a number of embodiments, $C_2$-$C_6$ alkenyl or alkynyl, or vinyl), oxiranyl, glycidyl, aryl, heterocyclyl, aralkyl, aralkenyl (aryl-substituted alkenyl, where aryl is as defined below, and alkenyl is vinyl which may be substituted with one or two $C_1$-$C_6$ alkyl groups and/or halogen atoms [in a number of embodiments, chlorine]), $C_1$-$C_6$ alkyl in which from 1 to all of the hydrogen atoms (in a number of embodiments 1) are replaced with halogen (in a number of embodiments, fluorine or chlorine where 1 or more hydrogen atoms are replaced, and in a number of embodiments, fluorine, chlorine or bromine where 1 hydrogen atom is replaced) and $C_1$-$C_6$ alkyl substituted with from 1 to 3 substituents (in a number of embodiments 1) selected from the group consisting of $C_1$-$C_4$ alkoxy, aryl, heterocyclyl, C(=Y)$R^{15}$, wherein $R^{15}$ is $C_1$-$C_{20}$ alkyl, $C_1$-$C_{20}$ alkoxy, aryloxy or heterocyclyloxy, and $R^{16}$ and $R^{17}$ are independently H, or $C_1$-$C_{20}$ alkyl, or $R^{16}$ and $R^{17}$ may be joined together to form an alkylene group of from 2 to 5 carbon atoms, wherein Y is N$R^{18}$ or O and $R^{18}$ is H, straight or branched $C_1$-$C_{20}$ alkyl or aryl and X may, for example, be generally any homolytically cleavable atom group or a group activated by degenerative radical exchange suitable for reversible deactivation radical polymerization. In a number of embodiments, X is selected from the group consisting of Cl, Br, I, nitroxyl, organotellurium, organostibine, organobismuthine, and —S—C(=S)—Z, wherein Z is selected from the group consisting of alkyl, alkoxy, alkylthio, aryl, and heteroaryl. Many different nitroxyl, organotellurium, organostibine, and organobismuthine groups as known in the art may be used herein for reversible deactivation radical polymerization. In a number of embodiments of organotellurium, organostibine, and organobismuthine groups, X is selected from the group consisting of —Te$R^{13}$, —Sb$R^{13}R^{14}$ and —Bi $R^{13}R^{14}$, wherein $R^{13}$ and $R^{14}$ are each independently selected from the group consisting of aryl or a straight or branched $C_1$-$C_{20}$ alkyl group. The nitroxyl group may be linked to the carbon through the oxygen radical forming an alkoxyamine.

Similar to X, the homolytically cleavable group or group activated by degenerative radical exchange of $R^{11}$ and $R^{12}$ can be generally any homolytically cleavable group or group activated by degenerative radical exchange suitable for reversible deactivation radical polymerization. In a number of embodiments, $R^{11}$, $R^{12}$ are each independently selected from the group consisting of Cl, Br, I, nitroxyl, organotellurium, organostibine, organobismuthine, —S—C(=S)—Z, H, $C_1$-$C_{20}$ alkyl, $C_3$-$C_8$ cycloalkyl, C(=Y)$R^{15}$, C(=Y)N$R^{16}R^{17}$, COCl, OH, CN, $C_2$-$C_{20}$ alkenyl, $C_2$-$C_{20}$ alkynyl, oxiranyl, glycidyl, aryl, heterocyclyl, aralkyl, aralkenyl, $C_1$-$C_6$ alkyl in which from 1 to all of the hydrogen atoms are replaced with halogen and $C_1$-$C_6$ alkyl substituted with from 1 to 3 substituents selected from the group consisting of $C_1$-$C_4$ alkoxy, aryl, heterocyclyl, C(=Y)$R^{15}$, C(=Y)N$R^{16}R^{17}$, oxiranyl and glycidyl. In general, whether it is desirable for either $R^{11}$ or $R^{12}$ to be a radical stabilizing group depends upon the nature of $R^2$ and/or L as well as the monomer(s) to be polymerized and can be readily determined by one skilled in the art.

In a number of embodiments, $R^{11}$ and $R^{12}$ are each independently selected from the group consisting of H, $C_1$-$C_{20}$ alkyl, aryl and a heterocycle. $R^{11}$ and $R^{12}$ may, for example, each independently selected from the group consisting of methyl, phenyl, pryidyl, substituted phenyl, substituted pyridyl and a heterocycle. In a number of embodiments, X is Br, $R^{11}$ is methyl and $R^{12}$ is methyl, and $R^2$ is

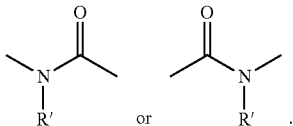

wherein R' is selected from the group of H, alkyl and aryl.

In a number of embodiments, the initiator or the transfer agent is bound to a phosphoramidite via a base stable linking group which is selected from the group consisting of

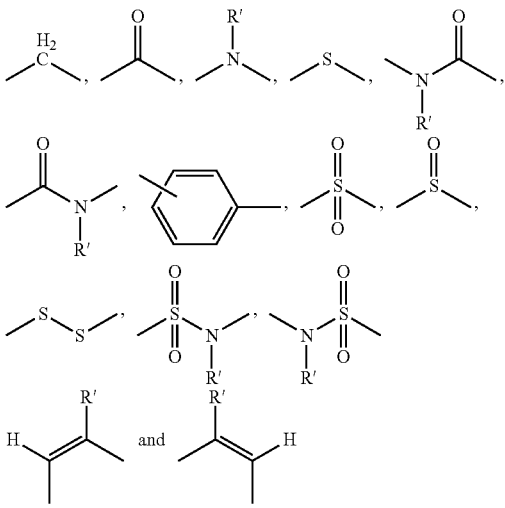

wherein where R' is selected from the group consisting of H, alkyl and aryl. The initiator or the transfer agent may, for example, be bound to a phosphoramidite via the base stable linking group which is

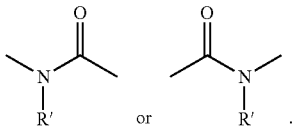

The phosphoramidite may, for example, be reacted with a free hydroxyl group of the end of the nucleotide chain assembly.

The polynucleotide may, for example, be synthesized via amidite coupling. The method hereof may further include removal of the polynucleotide from the solid support and deprotection of the polynucleotide.

The polymer may, for example, be grown from the initiator or from the site of the transfer agent under aqueous conditions or in the presence of a polar solvent. The polymer segment may, for example, be hydrophilic or water soluble. The polymer may also be grown from the initiator or from the site of the transfer agent under non-aqueous conditions. The polymer may, for example, be hydrophobic or water insoluble.

In a number of embodiments, the compound is attached at a 2'-position, a 5'-position or a 3'-position. In a number of embodiments, the initiator is an initiator for ATRP, RAFT, concurrent ATRP/RAFT or NMP. In the case of an ATRP initiator, the initiator for ATRP may be adapted to initiate a controlled ATRP in the presence of a catalyst complex formed with an excess of ligand under polymerization conditions wherein the polynucleotide is stable.

Solid phase supports used herein may, for example, include, but are not limited to, controlled pore glass and polystryrene.

In another aspect, a composition has the formula $R^1$-L-$(R^2\!-\!)_n\!-\!R^3$, wherein $R^1$ is a phosphoramidite, L is a base stable spacer group, wherein $R^2$ is a base stable linking group as defined above, wherein n is 0 or an integer in the range of 1 to 20, and $R^3$ is a residue of an initiator or a chain transfer agent for a reversible deactivation radical polymerization as defined above. As described above, the phosphoramidite may have the formula

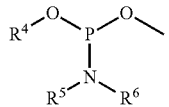

wherein $R^4$, $R^5$ and $R^6$ are as defined above. As also described above, in a number of embodiments, $R^3$ has the formula:

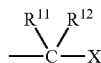

wherein X, $R^{11}$ and $R^{12}$ are as defined above.

In another aspect, a method of forming a composition for growth of a polymer via reversible deactivation radical polymerization therefrom includes attaching at least one initiator or at least one transfer agent for a reversible deactivation radical polymerization to a first compound by reacting a second compound with the first compound, the second compound having the formula $R^1$-L-$(R^2\!-\!)_n\!-\!R^3$, wherein $R^1$ is a phosphoramidite, L is a base stable spacer group, $R^2$ is a base stable linking group, wherein n is 0 or an integer in the range of 1 to 20, and $R^3$ is a residue of an initiator or a residue of a transfer agent for a reversible deactivation radical polymerization. $R^1$, L, $R^2$ and $R^3$ may be as defined above. The first compound may be immobilized upon a solid phase support. In a number of embodiments, the first compound is a biomolecule or a polynucleotide. The first compound may, for example, be selected from the group consisting of spermine, spermidine, a fluorescent dye, a dye quencher and biotin. In a number of embodiments, the first compound is a nucleotide chain assembly immobilized upon the solid phase support, and the second compound is reacted with an end of a nucleotide chain assembly during a solid phase synthesis of the polynucleotide.

In another aspect, a composition for growth of a polymer via reversible deactivation radical polymerization therefrom is formed by attaching at least one initiator or at least one transfer agent for a reversible deactivation radical polymerization to a first compound by reacting a second compound with the first compound. The second compound has the formula $R^1$-L-$(R^2\!-\!)_n\!-\!R^3$, wherein $R^1$ is a phosphoramidite, L is a base stable spacer group, $R^2$ is a base stable linking group, wherein n is 0 or an integer in the range of 1 to 20, and $R^3$ is a residue of an initiator for a reversible deactivation radical polymerization. $R^1$, L, $R^2$ and $R^3$ may be as defined above.

In a further aspect, a composition includes a phosphoramidite group covalently linked to a group including at least one initiator or at least one transfer agent for a reversible deactivation radical polymerization. The phosphoramidite group may be linked to the group including the at least one initiator or the at least one transfer agent via a linking group selected from the group consisting of

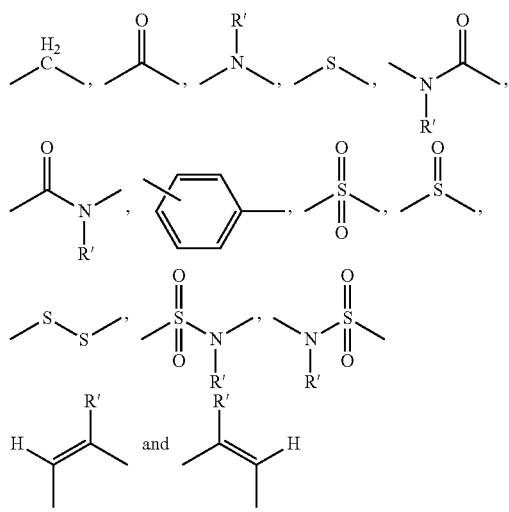

wherein where R' is selected from the group consisting of H, alkyl and aryl.

In a number of embodiments, the phosphoramidite group includes a functional group adapted to react with a target moiety to covalently bond a residue of the composition to the target moiety. The functional group may, for example, be a cyano group.

In still a further aspect, a method of synthesizing a composition includes reacting a phosphoramidite group with a compound including at least one initiator or at least one transfer agent for a reversible deactivation radical polymerization.

As used herein the terms "alkyl" (typically, $C_1$-$C_{20}$), "alkenyl" (typically, $C_2$-$C_{20}$)" and "alkynyl" (typically, $C_2$-$C_{20}$) refer to straight-chain or branched groups (except for $C_1$ and $C_2$ groups). "Alkenyl" and "alkynyl" groups may have sites of unsaturation at any adjacent carbon atom position(s) as long as the carbon atoms remain tetravalent, but, – or terminal (i.e., at the – and (–1)-positions) are present in a number of embodiments.

As used herein "aryl" refers to phenyl, naphthyl, phenanthryl, phenalenyl, anthracenyl, triphenylenyl, fluoranthenyl, pyrenyl, pentacenyl, chrysenyl, naphthacenyl, hexaphenyl, picenyl and perylenyl (preferably phenyl and naphthyl), in which each hydrogen atom may be replaced with alkyl of from 1 to 20 carbon atoms (preferably from 1 to 6 carbon atoms and more preferably methyl), alkyl of from 1 to 20 carbon atoms (preferably from 1 to 6 carbon atoms and more preferably methyl) in which each of the hydrogen atoms is independently replaced by a halide (preferably a fluoride or a chloride), alkenyl of from 2 to 20 carbon atoms, alkynyl of from 1 to 20 carbon atoms, alkoxy of from 1 to 6 carbon atoms, alkylthio of from 1 to 6 carbon atoms, $C_3$-$C_8$ cycloalkyl, phenyl, halogen, $NH_2$, $C_1$-$C_6$-alkylamino, $C_1$-$C_6$-dialkylamino, and phenyl which may be substituted with from 1 to 5 halogen atoms and/or $C_1$-$C_4$ alkyl groups. (This definition of "aryl" also applies to the aryl groups in "aryloxy" and "aralkyl.") Thus, phenyl may be substituted from 1 to 5 times and naphthyl may be substituted from 1 to 7 times (preferably, any aryl group, if substituted, is substituted from 1 to 3 times) with one of the above substituents. More preferably, "aryl" refers to phenyl, naphthyl, phenyl substituted from 1 to 5 times with fluorine or chlorine, and phenyl substituted from 1 to 3 times with a substituent selected from the group consisting of alkyl of from 1 to 6 carbon atoms, alkoxy of from 1 to 4 carbon atoms and phenyl. Most preferably, "aryl" refers to phenyl and tolyl.

In the context of the present invention, "heterocyclyl" refers to pyridyl, furyl, pyrrolyl, thienyl, imidazolyl, pyrazolyl, pyrazinyl, pyrimidinyl, pyridazinyl, pyranyl, indolyl, isoindolyl, indazolyl, benzofuryl, isobenzofuryl, benzothienyl, isobenzothienyl, chromenyl, xanthenyl, purinyl, pteridinyl, quinolyl, isoquinolyl, phthalazinyl, quinazolinyl, quinoxalinyl, naphthyridinyl, phenoxathiinyl, carbazolyl, cinnolinyl, phenanthridinyl, acridinyl, 1,10-phenanthrolinyl, phenazinyl, phenoxazinyl, phenothiazinyl, oxazolyl, thiazolyl, isoxazolyl, isothiazolyl, and hydrogenated forms thereof known to those in the art. Preferred heterocyclyl groups include pyridyl, furyl, pyrrolyl, thienyl, imidazolyl, pyrazolyl, pyrazinyl, pyrimidinyl, pyridazinyl, pyranyl and indolyl, the most preferred heterocyclyl group being pyridyl. Accordingly, suitable vinyl heterocycles to be used as a monomer in the present invention include 2-vinyl pyridine, 4-vinyl pyridine, 2-vinyl pyrrole, 3-vinyl pyrrole, 2-vinyl oxazole, 4-vinyl oxazole, 5-vinyl oxazole, 2-vinyl thiazole, 4-vinyl thiazole, 5-vinyl thiazole, 2-vinyl imidazole, 4-vinyl imidazole, 3-vinyl pyrazole, 4-vinyl pyrazole, 3-vinyl pyridazine, 4-vinyl pyridazine, 3-vinyl isoxazole, 3-vinyl isothiazoles, 2-vinyl pyrimidine, 4-vinyl pyrimidine, 5-vinyl pyrimidine, and any vinyl pyrazine, the most preferred being 2-vinyl pyridine. The vinyl heterocycles mentioned above may bear one or more (preferably 1 or 2) $C_1$-$C_6$ alkyl or alkoxy groups, cyano groups, ester groups or halogen atoms, either on the vinyl group or the heterocyclyl group, but preferably on the heterocyclyl group. Further, those vinyl heterocycles which, when unsubstituted, contain an N—H group may be protected at that position with a conventional blocking or protecting group, such as a $C_1$-$C_6$ alkyl group, a tris-$C_1$-$C_6$ alkylsilyl group, an acyl group of the formula $R^{10}CO$ (where $R^{10}$ is alkyl of from 1 to 20 carbon atoms, in which each of the hydrogen atoms may be independently replaced by halide, preferably fluoride or chloride), alkenyl of from 2 to 20 carbon atoms (preferably vinyl), alkynyl of from 2 to 10 carbon atoms (preferably acetylenyl), phenyl which may be substituted with from 1 to 5 halogen atoms or alkyl groups of from 1 to 4 carbon atoms, or aralkyl (aryl-substituted alkyl, in which the aryl group is phenyl or substituted phenyl and the alkyl group is from 1 to 6 carbon atoms), etc. (This definition of "heterocyclyl" also applies to the heterocyclyl groups in "heterocyclyloxy" and "heterocyclic ring.")

In general, any radically polymerizable alkene can serve as a monomer for polymerization. In a number of embodiments, monomers suitable for polymerization in the present method include those of the formula:

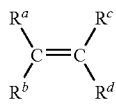

wherein $R^a$ and $R^b$ are independently selected from the group consisting of H, halogen, CN, straight or branched alkyl of from 1 to 20 carbon atoms (in a number of embodiments, from 1 to 6 carbon atoms, or from 1 to 4 carbon atoms) which may be substituted with from 1 to (2n+1) halogen atoms where n is the number of carbon atoms of the alkyl group (e.g. $CF_3$), unsaturated straight or branched alkenyl or alkynyl of 2 to 10 carbon atoms (in a number of embodiments, from 2 to 6 carbon atoms, or from 2 to 4 carbon atoms) which may be substituted with from 1 to (2n-1) halogen atoms (in a number of embodiments, chlorine) where n is the number of carbon atoms of the alkyl group (e.g. $CH_2=CCl-$), $C_3$-$C_8$ cycloalkyl which may be substituted with from 1 to (2n-1) halogen atoms (preferably chlorine) where n is the number of carbon atoms of the cycloalkyl group, $C(=Y)R^e$, $C(=Y)NR^fR^g$, $YC(=Y)R^e$, $SOR^e$, $SO_2R^e$, $OSO_2R^e$, $NR^hSO_2R^e$, $PR^e_2$, $P(=Y)R^e_2$, $YPR^e_2$, $YP(=Y)R^e_2$, $NR^h_2$ which may be quaternized with an additional $R^h$ group, aryl and heterocyclyl; where Y may be $NR^h$ S or O (preferably O); $R^e$ is alkyl of from 1 to 20 carbon atoms, alkylthio of from 1 to 20 carbon atoms, $OR^i$ (where $R^i$ is H or an alkali metal), alkoxy of from 1 to 20 carbon atoms, aryloxy or heterocyclyloxy; $R^f$ and $R^g$ are independently H or alkyl of from 1 to 20 carbon atoms, or $R^f$ and $R^g$ may be joined together to form an alkylene group of from 2 to 7 (preferably 2 to 5) carbon atoms, thus forming a 3- to 8-membered (preferably 3- to 6-membered) ring, and $R^h$ is H, straight or branched $C_1$-$C_{20}$ alkyl or aryl;

$R^c$ and $R^d$ are independently selected from the group consisting of H, halogen (preferably fluorine or chlorine), $C_1$-$C_6$ (preferably $C_1$) alkyl and $COOR^j$ (where $R^j$ is H, an alkali metal, or a $C_1$-$C_6$ alkyl group), or $R^a$ and $R^c$ may be joined to form a group of the formula $(CH_2)_{n'}$ (which may be substituted with from 1 to 2n, halogen atoms or $C_1$-$C_4$ alkyl groups) or $C(=O)-Y-C(=O)$, where n' is from 2 to 6 (in a number of embodiments 3 or 4) and Y is as defined above. In a number of embodiments, at least two of $R^a$, $R^b$, $R^c$ and $R^d$ are H or halogen.

The present systems, methods and compositions, along with the attributes and attendant advantages thereof, will best be appreciated and understood in view of the following detailed description taken in conjunction with the accompanying drawings.

DETAILED DESCRIPTION

Figure 1A:
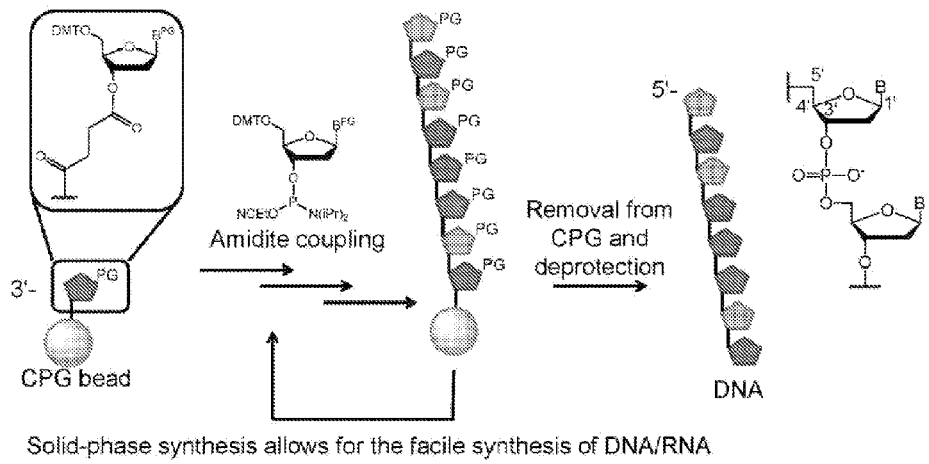
FIG. 1A illustrates schematically the solid phase synthesis of polynucleotides.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an initiator group or functionality" includes a plurality of such initiator groups or functionalities and equivalents thereof known to those skilled in the art, and so forth, and reference to "initiator group or functionality" is a reference to one or more such initiator groups or functionalities and equivalents thereof known to those skilled in the art, and so forth. Recitation of ranges of values herein are merely intended to serve as a shorthand method of referring individually to each separate value falling within the range. Unless otherwise indicated herein, each separate value, as well as intermediate ranges, are incorporated into the specification as if individually recited herein. All methods described herein can be performed in any suitable order unless otherwise indicated herein or otherwise clearly contraindicated by the text.

The following abbreviations are used herein:
Deoxyribonucleic acids (DNA)
Ribonucleic acids (RNA)
Nucleic acid-polymer hybrids (NAPH)
Deoxyribonucleic acid block copolymer (DNABCp)
Reversible deactivation radical polymerization (RDRP)
Atom transfer radical polymerization (ATRP)
Nitroxide mediated polymerization (NMP)
Reversible addition fragmentation transfer (RAFT)
Bromoisobutyrate (iBBr)
Gel permeation chromatography (GPC)
Controlled pore glass (CPG)
Oligo(ethylene oxide) methacrylate (OEOMA, $M_n$=475)
Rhodamine methacrylate (RMA)
Fluorescence resonance energy transfer (FRET)
N,N,N',N'',N''-pentamethyldiethylenetriamine (PMDETA)
Ethylene glycol diacrylate (EGDA)
Copper sulfate pentahydrate ($CuSO_4.5H_2O$)
Acetonitrile (ACN)
N,N-Diisopropylethylamine (DIPEA)
Matrix-Assisted Laser Desorption/Ionization-Time Of Flight (MALDI-TOF)
Grafting from ('g-f')
Blocking from ('b-f')

In a number of representative embodiments hereof, strategies for the preparation of polynucleotide-polymer hybrids by chain-extending from an initiator incorporated into one or more specific units of the polynucleotide are set forth. Polynucleotides including one or more incorporated initiators are sometimes referred to herein as polynucleotide macroinitiators. Examples of suitable polynucleotides include, but are not limited to, polynucleotides and oligonucleotide sequences, including DNA, RNA, DNA/RNA hybrids and derivative or analogs thereof, which may be double stranded or single stranded and include, without limitation, synthetic polynucleotides that may be administrated to a patient.

The term "polymer" or the prefix "poly" (when referring to a particular type of polymer such as a polynucleotide) refers generally to a molecule, the structure of which includes repeat units derived, actually or conceptually, from molecules of low relative molecular mass (monomers). The term "oligomer" or the prefix "oligo" (when referring to a particular type of oligomer such as an oligonucleotide) refers generally to a molecule of intermediate relative molecular mass, the structure of which includes a small plurality of units derived, actually or conceptually, from molecules of lower relative molecular mass (monomers). In general, a polymer is a compound having >1, and more typically >13 repeat units or monomer units, while an oligomer is a compound having >1 and <20, and more typically less than 13 repeat units or monomer units.

In other representative embodiments, compounds hereof include at least one initiator functionality and at least one reactive functionality for reaction with a polynucleotide or other molecule (for example, a biomolecule) to incorporate the initiator functionality into the polynucleotide or other molecule. The initiator functionality can be incorporated into a polynucleotide or other molecule immobilized upon a support or to a polynucleotide or other molecule in solution. In a number of embodiments, initiator functionality is covalently bound within the compound including the imitator functionality via a linkage which is stable under either solid phase or solution phase conditions. For example, the linkage group may be stable under solid phase polynucleotide synthesis, including deprotection and detachment/removal. For example, an immobilized functional DNA macroinitiator may chain extended, and the purification process for resultant formed DNA bock copolymer (DNABCp) is simple and complete. In a number of representative examples, described herein a Cy5-3'-DNA-iBBr dual functional DNA macroinitiator is chain extended and the purification process for the formed DNA bock copolymer (DNABCp) is simple and complete.

In a number of representative embodiments of "grafting-from" or "blocking-from" reactions hereof, the reactions are conducted by polymerizing (co)monomers from an initiator functionality introduced into a specific site during solid phase synthesis of a polynucleotide, and hence present in every polynucleotide molecule, via, for example, a phosphoramidite moiety including at least one polymerization initiator functionality. The "grafting-from", chain extension reactions hereof provide several advantage compared to "grafting-to" procedures including simplified purification procedures, including removal of low molecular weight catalyst, monomers, and solvent from a relatively high molecular weight, designed bio-conjugate. Furthermore, the "grafting-from" procedures hereof provide higher yields of a well-designed bio-conjugate than achievable in "grafting to" procedures as a result of less steric hindrance associated with addition of a low molecular weight monomer to a functionalized polynucleotide or other molecule compared to the physical limitations of conducting conjugation of two large macromolecules (for example, a biomolecule and a preformed polymer).

Further, the "grafting-from" procedures hereof provide efficient access to a wide variety of bioconjugates with higher yields and greater efficiency than existing "grafting from" bioconjugation procedures and overcome significant limitations of existing procedures by providing a method for efficient site specific incorporation of RDRP initiator(s), and/or other desired functionality (see, for example, U.S. Pat. No. 6,114,518), into, for example, a polynucleotide and development of efficient conditions for the grafting/blocking from copolymerization reactions utilizing RDRP procedures.

In a number of representative embodiments, the procedure used for incorporation of a radically transferable atom or group into the terminal unit of a nucleotide chain assembly of, for example, a synthesized DNA or RNA molecule, can be used to incorporate any desired functionality into any selected unit in a synthetic polynucleotide wherein the functionality can be selected for any envisioned subsequent material modification procedure including direct grafting/blocking-from polymerization or further functionalization to allow different grafting/blocking-from polymerization or tethering procedures. The procedures hereof enable, for example, formation of DNAPH including one or more segments of well-defined synthetic copolymers conjugated to DNA. Representative DNAPH delivery systems synthesized using, for example, ATRP offer customizable and tunable structure for precise targeted delivery of active nucleic acid molecules.

As described above, the most common RDRP methods are ATRP, NMP RAFT, and degenerative transfer, each of which allow unprecedented control over polymer properties. See, for example, Matyjaszewski, K., Davis, T. P., Eds. Handbook of Radical Polymerization; Wiley: Hoboken, 2002 chapter 11 pp 523-628; Matyjaszewski, K.; Xia, J. *Chem. Rev.* 2001, 101, 2921-2990; Braunecker, W. A.; Matyjaszewski, K. *Progress in Polymer Science* 2007, 32, 93-146; Siegwart, D. J.; Oh, J. K.; Matyjaszewski, K. *Prog. Polym. Sci.* 2012, 37, 18-37; Hawker, C. J.; Bosman, A. W.; Harth, E. *Chemical Reviews* 2001, 101, 3661-3688; Moad, G.; Rizzardo, E.; Thang, S. H. *Aust. J. Chem.* 2012, 65, 985-1076, the disclosures of which are incorporated by reference. Degenerative transfer procedures have also been utilized as discussed in Tasdelen, M. A. et al., Telechelic Polymers by Living and Controlled/Living Polymerization Methods, *Prog. Polym. Sci.* 2011, 36, 455-567.

ATRP is the most efficient RDRP method for the preparation of pure segmented bio-conjugates. Unlike RAFT, ATRP does not require addition of a radical initiator to continuously form new polymer chains that do not contain the desired α-biofunctional group in a "grafting from" reaction. However, as disclosed in U.S. Pat. No. 8,445,610, an ATRP catalyst complex can be used to activate a RAFT reaction and overcome this limitation. Unlike NMP or stable free radical polymerization (SFRP), ATRP does not require high temperatures to generate the active species by homolytic cleavage of the dormant chain end. ATRP allows the synthesis of novel α-, ω-telechelic multi-segmented copolymers with a predetermined degree of polymerization (DP), low molecular weight distribution ($M_w/M_n$), incorporating a wide range of functional monomers and displaying controllable macromolecular architectures, all under mild reaction conditions.

ATRP was thus used in a number of representative studies hereof as an exemplary RDRP procedure. In a number of embodiments, bioresponsive polymer conjugates can be prepared at low temperatures and without the presence, or formation, of undesired impurities as a result of the use of free radical initiators. As described further below, ATRP procedures that proceed under biologically compatible conditions as exemplified in WO2013/028756 and Averick et al.; *ACS Macro Lett.* 2012, 1, 6-10, the disclosure of which are incorporated herein by reference, were used in a number of embodiments hereof. Such procedures overcome limitations inherent in aqueous ATRP. See, for example, Matyjaszewski, et al Macromolecules, 2004, 37 (26), pp 9768-9778, the disclosure of which is incorporated herein by reference. ATRP procedures with higher concentrations of catalyst, predominately in the deactivator oxidation state, can be employed with no observable damage to the DNA macroinitiator.

When conducting an ATRP, the functionalities initially present on the introduced initiator are preserved and fragments of the initial initiator form both the α- and ω-chain end units on the controllably synthesized polymer segment. The polymers synthesized using ATRP show tolerance towards many functional groups, such as hydroxy, amino, amido, esters, carboxylic acid, that may be incorporated into a copolymer and then, for example, used for post-polymerization modifications, including covalent linking of biomolecules and molecules for drug delivery.

A schematic illustration of solid phase synthesis of nucleic acids via amidite coupling is provided in FIG. 1A. In general, naturally occurring nucleotides (nucleoside-3'- or 5'-phosphates) and their phosphodiester analogs are insufficiently reactive to provide a synthetic route to preparation of oligonucleotides in high yields. The rate of the formation and selectivity of internucleosidic linkages is improved using phosphoramidite derivatives of nucleosides or nucleoside phosphoramidites as building blocks in polynucleotide synthesis. In such solid phase syntheses, all other functional groups present in nucleosides are rendered unreactive by attaching protecting groups to prevent undesirable side reactions. Upon the completion of the polynucleotide chain assembly, all of the protecting groups are removed to yield the desired polynucleotides.

One challenge that had to be overcome to provide viable new methods for preparing polynucleotide-polymer conjugates was to design compounds or molecules including an initiator group or other desired functionality that could be incorporated into a polynucleotide molecule such as DNA or RNA in a site specific manner in high yield. Moreover, to prepare relatively large amounts of functional polynucleotides, exemplified by incorporation of an initiator functionality that allows conducting a range of screening polymerization conditions, the methodology should be compatible with solid phase polynucleotide synthesis. Functional groups or small molecules may be attached to polynucleotides via phosphoramidite coupling chemistry. However, the incorporated functional group or small molecule, needs to be stable under the nucleic acid deprotection conditions (that is, exposure to ammonium hydroxide at room temperature for approximately 4 h). As used herein, the term "base stable" refers to stability in the presence of ammonium hydroxide at room temperature for 4 h.

Figure 1B:
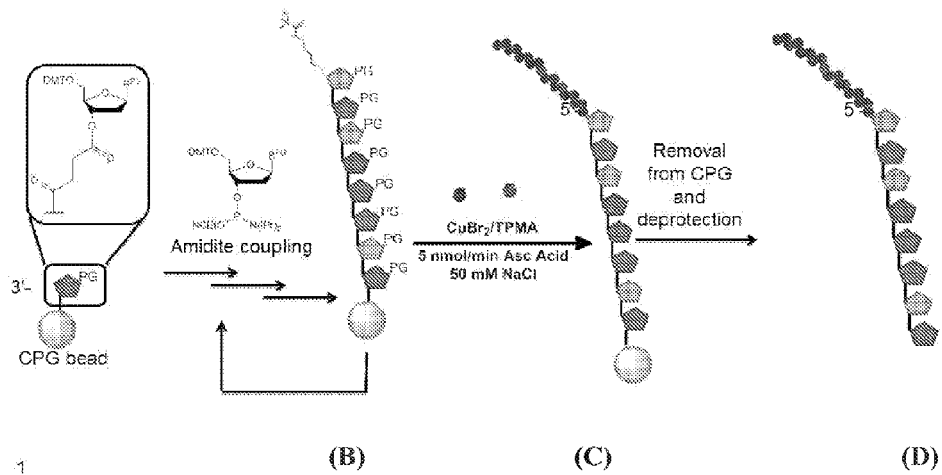
FIG. 1B illustrates schematically incorporation of initiating functionality forming 5'-iBBr-DNA, (molecule (B) in FIG. 1B) and formation of a DNA-b-copolymer conjugate (molecule (C) in FIG. 1B) prior to removal from CPG bead and deprotection, (to obtain molecule (D) in FIG. 1 B).

A representative example of the site-specific incorporation a representative ATRP initiating functionality into a DNA molecule by reaction of a phosphoramidite compound including the initiating functionality with the end group of the growing nucleotide chain assembly is illustrated in FIG. 1B. The schematic illustration of FIG. 1B shows incorporation of the functionalized phosphoramidite, comprising the ATRP initiating functionality, forming 5'-iBBr-DNA (molecule (B) in FIG. 1B) in high yield and formation of a DNA-b-copolymer conjugate (molecule (C) in FIG. 1B) prior to removal of the nucleic acid from the controlled pore glass (CPG) bead and deprotection, (molecule (D) in FIG. 1B). The general methodology represented in FIG. 1B facilitates the rapid preparation of the bioconjugate as well as the ready purification of the functional bioconjugates from the unreacted monomers and catalyst.

The fundamental, four-component ATRP process includes the addition, or in situ formation, of an initiator, in this case a molecule with a transferable atom or group that is completely incorporated into the final product with fragments of the first initiator molecule present at the α- and ω-chain ends of the formed polymer, a transition metal and a ligand, that form, a partially soluble transition metal complex that participates in a reversible redox reaction with the added initiator or a dormant polymer to form the active species to copolymerize radically polymerizable monomers. The ATRP process, components thereof, and a number of improvements to the basic ATRP process are, for example, described, in the following commonly assigned patents and patent applications: U.S. Pat. Nos. 5,763,548; 5,807,937; 5,789,487; 5,945,491; 6,111,022; 6,121,371; 6,124,411; 6,162,882; 6,624,262; 6,407,187; 6,512,060; 6,538,091; 6,541,580; 6,624,262; 6,627,314; 6,759,491; 6,790,919; 6,887,962; 7,019,082; 7,049,373; 7,064,166; 7,125,938; 7,157,530; 7,332,550; 7,407,995; 7,572,874; 7,678,869; 7,795,355; 7,825,199; 7,893,173; 7,893,174; 8,252,880; 8,273,823; 8,349,410; 8,367,051; 8,404,788, 8,445,610, U.S. patent application Ser. Nos. 12/877,589; 12/949,466 and PCT International Patent Application Nos. PCT/US04/09905; PCT/US06/33152; PCT/US2006/048656; PCT/US08/64710; PCT/US09/36377; PCT/US2010/029073; PCT/US2011/05104; PCT/US11/65578 and PCT/US12/051855, the disclosures of which are incorporated herein by reference.

Figure 1C:
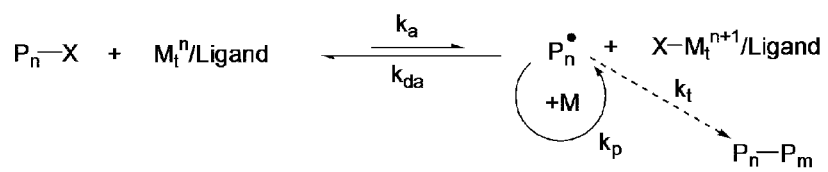
FIG. 1C illustrates a generally accepted mechanism of an ATRP reaction.

Without limitation to any mechanism, the generally accepted mechanism of an ATRP reaction is illustrated in FIG. 1C. Typically, ATRP processes comprise a transition metal complex. The transition metal complex may participate in a repetitive redox reaction homolytically removing a radically transferable atom or group from an initiator molecule or dormant polymer chain, $P_{n-}$, to form the active propagating species, $P^{\bullet}{}_{n}$, and then deactivating active propagating species, $P^{\bullet}{}_{n}$, by donating back a transferable atom or group. The transition metal catalyst for this repetitive addition process must be present, at least partially, in the lower oxidation state, or activator state, $M_f^n$/Ligand. Any transition metal complex capable of maintaining the dynamic equilibrium and participate in a redox reaction comprising the transferable atom or group with the polymer chain may be used as the catalyst in ATRP, and many examples are discussed in the cited art. A suitable equilibrium can be formed after consideration of oxidation states, complex formation with suitable ligands and redox potential of the resulting complex to provide a catalyst for the desired (co)polymerization of a wide range of (co)monomers. A wide variety of ligands have been developed to prepare transition metal catalyst complexes that display differing solubility, stability and activity.

In a number of representative studies, CPG beads with a protected iBBr-DNA1 sequence were suspended in the polymerization medium and a polymerization was conducted in situ using 5% monomers (OEOMA and RMA) and 1.7% Cu and after extensive washing of the CPG beads with water to remove any unreacted monomer and catalyst. After polymerization, the beads were bright red, indicating copolymer growth from the DNA initiator on the solid support. Cleavage from the CPG beads and removal of the protecting groups of the DNA bases using standard DNA deprotection conditions yielded the DNABCp. The DNABCp was analyzed using GPC, which indicated a molar mass of $M_n$=205 kDa and $M_w/M_n$=1.43.

Compared to previously reported activated ester couplings that are performed in solution phase following DNA synthesis, deprotection and purification, the present method offer simplified access and greater yield of the NA functionalized with an initiator. In a number of embodiments, the methods disclosed herein allow for simple site specific conjugation of a polymer to a polynucleotide and simple purification of the formed product by washing of low molecular molecules from the formed conjugate, thereby providing high yields of the high purity (co)polymer functionalized polynucleotide.

Figure 2:
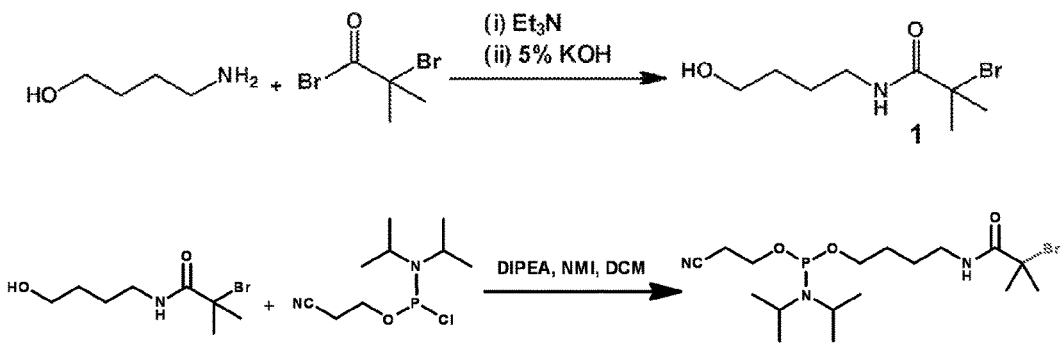
FIG. 2 illustrates and embodiment of a synthetic scheme for synthesizing a phosphoramidite including a functional residue of a reversible deactivation radical polymerization initiator.

A representative scheme for the synthesis of the phosphoramidite compound containing an ATRP initiator functionality iBBR that is capable of surviving deprotection conditions using ammonia at 60° C. is illustrated in FIG. 2. The functional phosphoramidite compound was prepared using commonly available commercial reagents in a two-step procedure forming a stable amide link between the initiating functionality and the phosphoramidite in good yields. This procedure may, for example, be employed to incorporate a multiplicity of different functional groups, including groups known to participate in high yield linking chemistries, into the incorporable phosphoramidite prior to incorporation into nucleic acid molecules at any selected cite within the nucleic acid. Groups know to participate in high yield linking chemistries are, for example, disclosed in PCT International Patent Publication NO. WO2005/087818, the disclosure of which is incorporated herein by reference.

In a number of embodiments, the compounds used to incorporate an initiating functionality into an oligonucleotide have the formula $R^1$-L-$(R^2—)_n$—$R^3$, wherein $R^1$ comprises a group adapted to react with the end of the nucleotide chain assembly, L is a base stable spacer group, none, wherein $R^2$ is a base stable linking group, wherein n is 0 or an integer in the range of 1 to 20, and $R^3$ is a residue of an initiator for a reversible deactivation radical polymerization. Examples of suitable groups to react with the end of the nucleotide chain assembly include a phosphoramidite group, an azide group, an alkyne group, an N-hydroxysuccinimide ester group, a maleimide group, a dibromomaleimide group or a thiol group. As described above, the spacer group L may have the formula:

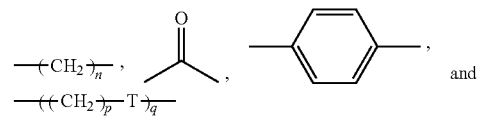

As described above, the base stable linking group $R^2$ may have the formula:

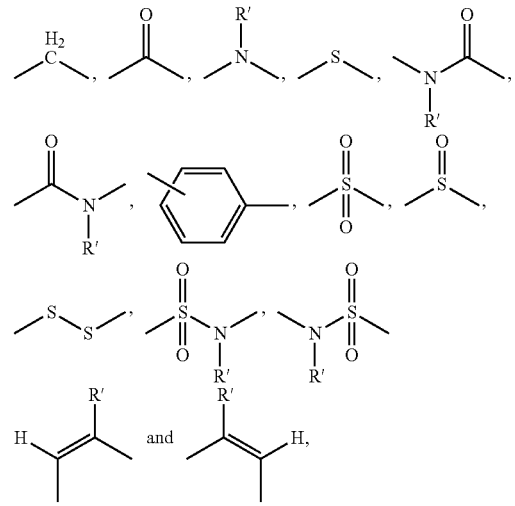

and $R^3$ is the residue of an initiator group as also described above. Compounds having the formula $R^1$-L-$(R^2-)_n-R^3$ may be readily synthesized using the general procedure outlined in FIG. 2.

Figure 3A:
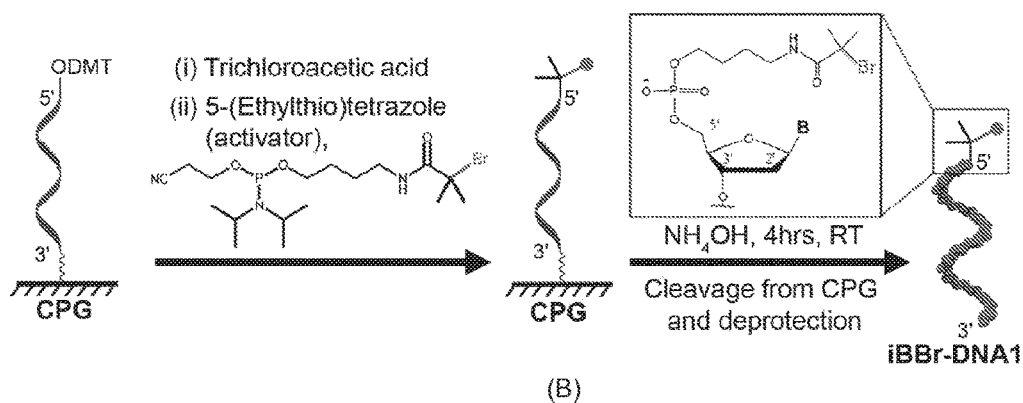
FIG. 3A illustrates an embodiment of a solution phase synthesis of a representative DNA macroinitiator.
Figure 4A:
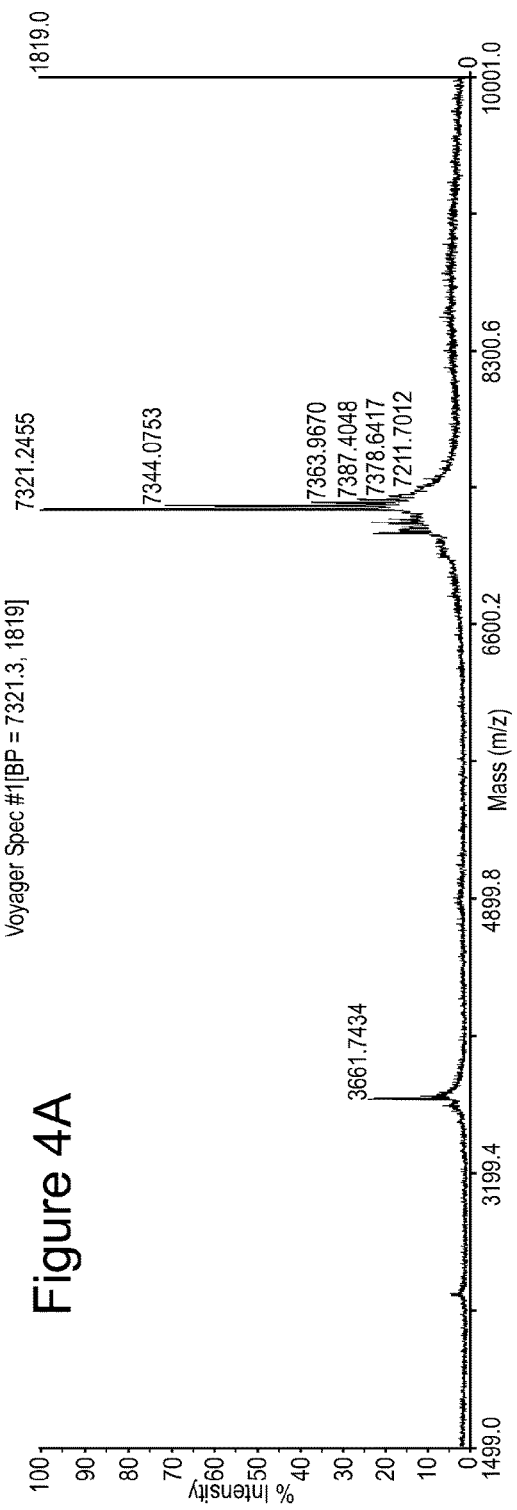
FIG. 4A illustrates MALDI-TOF analysis of SeqA-iBBr (Expected mass: 7320.2, Mass Found: 7321.25 (M+H⁺)).

In a number of embodiments, the phosphoramidite initiator was incorporated into the terminal unit in a 23-mer DNA sequence in a 1 micromole scale amidite coupling synthesis of the nucleic acid. The first step in the procedure is illustrated in in FIGS. 1B and 3A, forming molecule (B). In a number of studies, the DNA comprising the ATRP initiating functionality was then removed from the CPG and deprotected. Successful incorporation of the initiator functionality into the DNA was confirmed using MALDI-TOF as illustrated in the spectrum of FIG. 4A.

After removal of the 5'-ODMT (dimethoxytrityl) protecting group from the DNA (in the CPG bead), the ATRP initiator phosphoramidite was conjugated to the 5'-OH group. Cleavage from the solid support and removal of the base protecting groups and cyanoethyl groups using standard conditions gave the DNA conjugated to the ATRP initiator (iBBr-DNA1 in FIG. 3A).

Figure 3B:
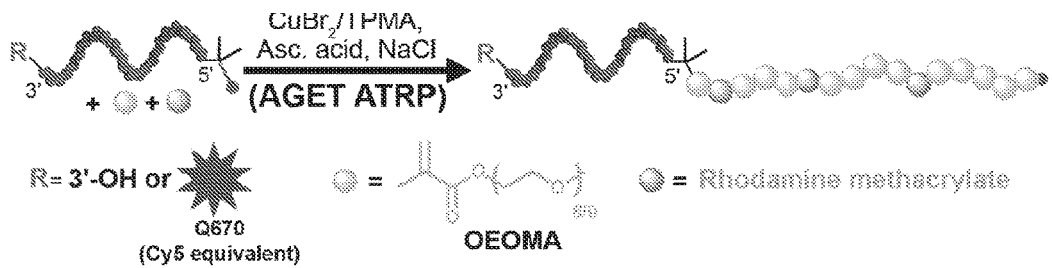
FIG. 3B illustrates solution phase synthesis of a representative DNA-polymer hybrid in a growing-from procedure using the DNA macroinitiator of FIG. 3A.

Direct synthesis of a DNA-polymer conjugate in solution phase by AGET ATRP using the initiator modified DNA is illustrated in FIG. 3B. Two different initiator modified DNA's, one with 3'-OH and one with a 3'-QUASOR® 670 or 3'-Q670 dye, were used to synthesize polymers with a mixture of OEOMA and rhodamine methacrylate as the monomers. The 3'-Q670 modification incorporates a fluorescent dye at the 3' terminus of an oligonucleotide. 5' The QUASAR 670 fluorophore is an indocarbocyanine dye which fluoresces in the red region of the visible spectrum and is available from Biosearch Technologies of Petaluma, Calif.

The representative DNA sequence used in a number of studies was 5'-gca ct gca gtt gga tcc cat agc-3', and the DNA-initiator or DNA macroinitiator conjugate is referenced SeqA-iBBr herein. In a number of representative studies, incorporation of a phosphoramidite further including a functionality for initiation of an ATRP (that is, a functional residue of an ATRP initiator) was effected at the terminus of the DNA strand. However, the functionality may be incorporated within any desired sequence during the polynucleotide synthesis. In embodiments, in which a phosphoramidite-initiator conjugate is used, the phosphoramidite-initiator conjugate can be reacted with an available hydroxyl group on a nucleotide in the sequence. The preparation of the ATRP phosphoramidite DNA macroinitiator, using controlled pore glass (CPG) beads for solid phase initiator incorporation, with the SeqA-iBBr grown from the surface affords rapid purification and higher yields of the DNA initiator, compared, for example, to previously reported, solution-phase activated ester couplings of initiator functionality onto DNA.

An Activator Generated by Electron Transfer (AGET) ATRP procedure was used as a starting point to evaluate a range of conditions to determine how to best control the blocking from copolymerization. See, *ACS Macro Lett.* 1(1): 6-10. AGET ATRP has several advantages over traditional ATRP including using oxidatively stable copper/ligand complexes, control over the reaction rate by controlling the feed rate of the reducing agent to activate a fraction of the added catalyst complex, and control over the rate of polymerization in addition to lowering the total copper concentration. AGET ATRP is a powerful yet convenient method to prepare, for example, block-copolymers, and was used to screen a range of polymerization conditions to determine the optimal parameters to prepare well defined DNAPH's. However, because of low reaction volumes, typically 50 microliters, determination of monomer conversion was not possible. Nonetheless, direct analysis of the final block copolymers molecular weight and molecular weight distributions could readily be obtained using GPC.

AGET was selected as the starting point in a number of studies hereof as the low amounts of SeqA-iBBr initially available presented scaling problems when lower amounts of catalyst were targeted. However, Activator ReGenerated by Electron Transfer (ARGET) ATRP may be used when larger scale preparations are targeted. See, for example, *Macromolecules*, 2012, 45(16): 6371-6379. Another recently developed approach to initiation of an ATRP reaction which may be used in the polymerization reactions hereof is photoinitiated ATRP, wherein light is used to reduce the $Cu^{II}$ to generate a $Cu^{I}$-complex with no byproducts. The ARGET ATRP procedure may also be used to, for example, prepare pure nucleic acid hybrids. See, for example, *ACS Macro Lett.* 2012, 1, 1219-1223.

To develop suitable conditions for block copolymer growth from the DNA SeqA-iBBr, the concentration of the initiator and feed rate of the reducing agent were kept constant while varying several key reaction parameters, such as reaction time, catalyst, monomer and salt concentration. The addition of NaCl to the reaction enhances the concentration of the deactivator present on the reaction medium leading to a better control over the polymerization. The NaCl concentration was varied from 50 to 300 mM. Another varied parameter was the concentration of the catalyst, $CuBr_2$:TPMA (1:8), which was varied from ~0.9% to ~4.5% (by mole to monomer). The targeted degrees of polymerization were from ~100 to ~500, and the total reaction times varied from 0.5 to 2 hours The results are presented in Table 1.

TABLE 1

| Entry | M/RhMA/ I/TPMA/ $CuBr_2$ | $FR_{AA}$, nmol/min | NaCl mM | $Cu^a$ ppm | Time m | Conv. % | $I + M_{n\,th}{}^b$ ×10$^{-3}$ | $M_{n\,GPC}{}^c$ ×10$^{-3}$ | $M_w/M_n$ |
|---|---|---|---|---|---|---|---|---|---|
| 1 | 496/2/1/4.2/34.3 | 5 | 50 | 8600 | 120 | n/a | 250 | 108 | 3.5 |
| 2 | 496/2/1/8.5/68.5 | 5 | 50 | 17000 | 120 | n/a | 250 | 201 | 1.36 |
| 3 | 198/2/1/4.2/34.3 | 5 | 50 | 22000 | 60 | n/a | 105 | 108 | 1.12 |
| 4 | 198/2/1/4.2/34.3 | 5 | 50 | 22000 | 30 | n/a | 105 | 110 | 1.14 |
| 5 | 198/2/1/4.2/34.3 | 5 | 300 | 22000 | 60 | n/a | 105 | No polymer | |
| 6 | 198/2/1/4.2/34.3 | 5 | 100 | 22000 | 60 | n/a | 105 | 83 | 1.48 |
| 7 | 99/2/1/4.2/34.3 | 5 | 50 | 43000 | 60 | n/a | 58 | 63 | 1.24 |

Figure 5:
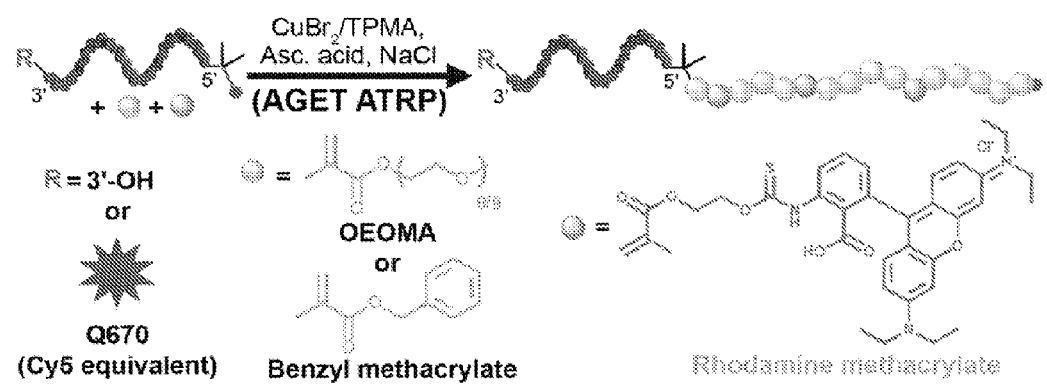
FIG. 5 illustrates schematically grafting-from functionalized DNA using AGET ATRP and incorporation of rhodamine containing comonomer.

The monomers chosen for the blocking from SeqA-iBBr copolymerization were oligo(ethylene oxide) methacrylate (OEOMA, $M_n$=475). In general OEOMA monomers are available in higher purity than other commercially available biocompatible oligo(ethylene oxide) methacrylates. A small percent of rhodamine methacrylate (RMA) was also incorporated into the reaction mixture to facilitate visualization of the product and enhance the ability to characterize the DNAPH as illustrated in FIG. 5.

Figure 6:
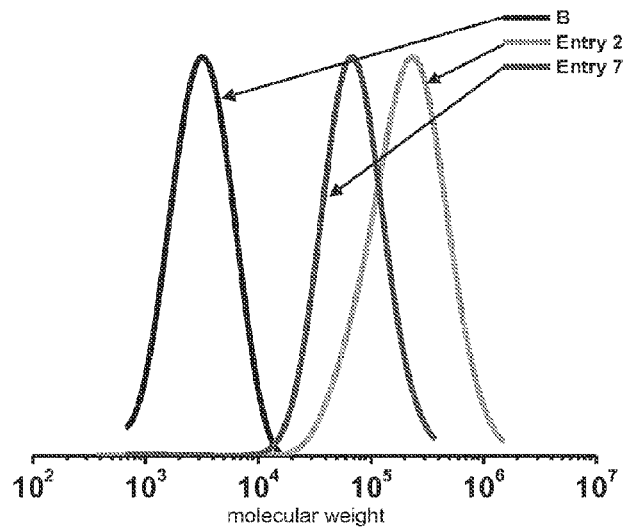
FIG. 6 illustrates GPC traces for the SeqA-iBBr nucleic acid macroinitiator and grafting from conjugates prepared under the conditions (summarized in Entries 2 and 7 in Table 1 hereof).

Using the reaction conditions identified in Table 1, well-defined polymers could be grown from SeqA-iBBr, which was confirmed by directly analyzing the samples using GPC. FIG. 6 sets forth GPC traces of the macroinitiator and samples prepared in two blocking-from ATRP reactions (Entries 2 and 7 from Table 1). The molecular weight and molecular weight distribution of the DNA-polymer hybrids could be determined, allowing determination of optimized conditions that led to well-defined DNAPH including polymer segments with predetermined molecular weights and low molecular weight distributions.

Figure 4B:
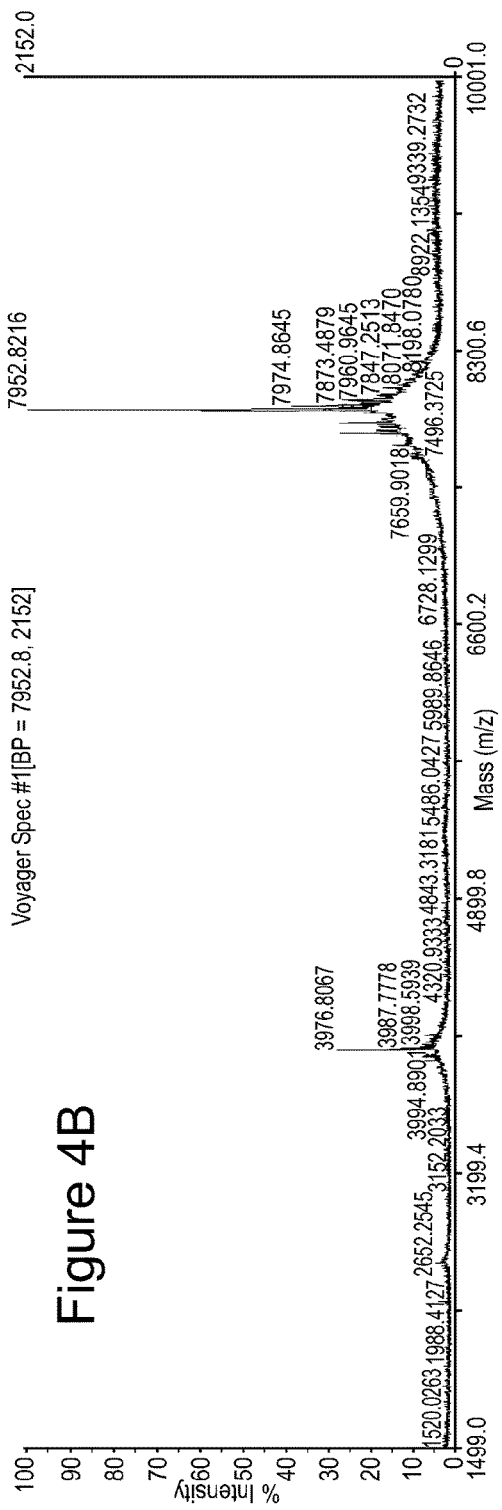
FIG. 4B illustrates MALDI-TOF analysis of Cy5 3'-SeqA-iBBr (Expected mass: 7320.2, Mass Found: 7952.8 (M+H⁺)).
Figure 7A:
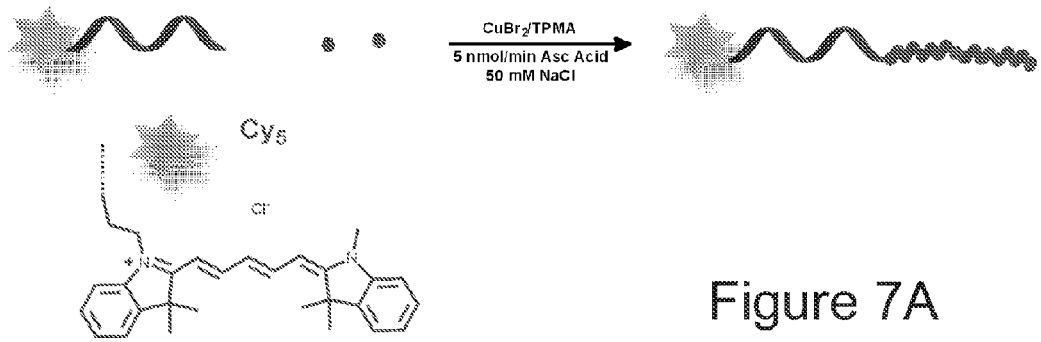
FIG. 7A illustrates schematically block copolymer synthesis from Cy5-DNA-iBBr.

To confirm that the DNA had not been modified in any manner by conducting an ATRP from the SeqA-iBBr a DNA initiator with a Cy5-3' end and a 5' ATRP initiator was prepared by utilizing a Cy5 functionalized bead and a functional block copolymer was prepared by growing a copolymer of OEOMA and rhodamine-MA from the DNA initiator. See FIGS. 7A and 7B. FIG. 4B shows the MALDI-TOF-Cy5 3'-SeqA-iBBr. The expected mass of 7320.2, was very close to the mass found: 7952.8 (M+H$^+$).

Figure 8:
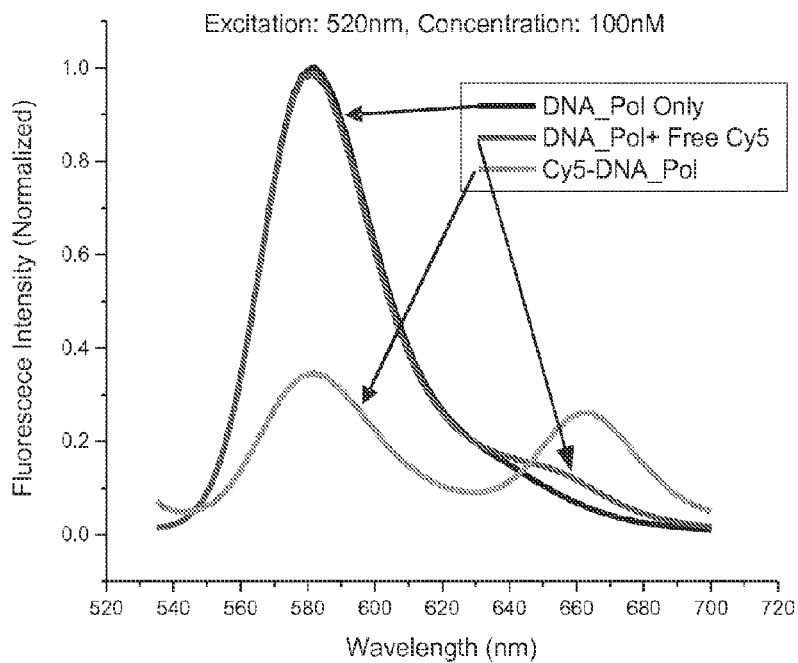
FIG. 8 illustrates Førster resonance energy transfer or fluorescence resonance energy transfer (FRET) characterization of DNA confirming the integrity of the DNA after block copolymer growth, wherein the emission spectra of DNA-b-POEOMA-co-Rhodamine MA, DNA-b-POEOMA-co-Rhodamine MA+Cy 5, Cy5-DNA-b-POEOMA-co-Rhodamine MA were measured concentrations at 100 nM.

The synthesis of the segmented copolymer with incorporated rhodamine allowed confirmation that the Cy5 DNA was intact and the polymer uniformly tethered to the DNA by using fluorescence resonance energy transfer (FRET) analysis of the signals of the rhodamine and the Cy5. FRET analysis is a distance-dependent interaction between the electronic excited states of two dye molecules in which excitation is transferred from a donor molecule to an acceptor molecule without emission of a photon. If the DNA had been degraded during the polymerization the Cy5 unit would have been be removed from the Cy5-chain end during purification (dialysis) and its signal would be lost. By growing OEOMA-rhodamine copolymers a FRET study could be undertaken to determine if the copolymer segment can undergo FRET with the Cy5 DNA. If FRET transfer was observed it would mean that the DNA was intact. The reaction mixture was purified using dialysis with a 25 k MWCO limit into ultra-pure water with five solvent exchanges to ensure high sample purity (i.e. no free Cy5 or RMA). This SeqA integrity test employed FRET from the block copolymer's RMA units to the 5'-Cy5. Since the two dyes would be in relatively close proximity FRET transfer would occur if the samples were covalently attached. Control studies of direct Cy5 excitation at 520 nm and simply mixing equimolar concentrations of free Cy5 and SeqA-b-POEOMA-co-RMA did not lead to a FRET transfer while the Cy5-SeqA-b-POEOMA-co-RMA had excellent FRET, as is shown in FIG. 8, which indicates that the DNA did not degrade during polymerization. The retention of the Cy5 DNA chain end was also confirmed using fluorescence spectroscopy. Furthermore, polymer conjugation to the DNA was further confirmed using the control experiment where Cy5 was simply mixed with a DNA-block-POEOMA-co-rhodamine and minimal FRET transfer was observed, at equimolar concentrations.

Figure 9:
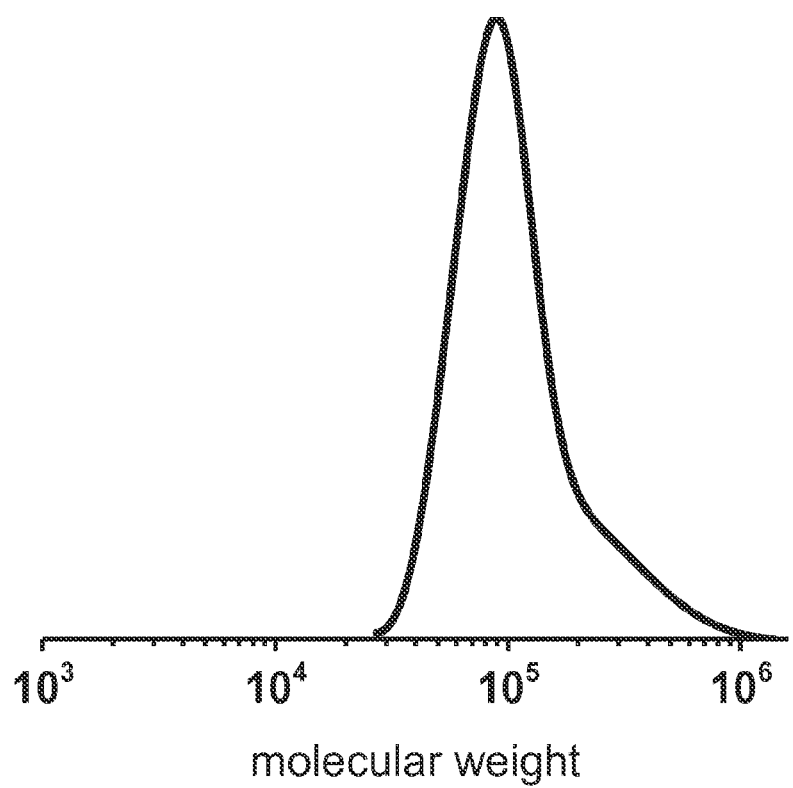
FIG. 9 illustrates a GPC spectrum of the DNAPH formed by directly grafting-from SeqA-iBBr on controlled pore glass bead.

In other representative studies, solid phase DNA synthesis was employed to prepare w-functionalized DNA macroinitiator with high purity and in high yield as described above. The immobilized macroinitiator was used in a blocking-from polymerization to form segmented DNA polymer hybrid copolymers. As described above, synthetic nucleic acids are, primarily, prepared using solid phase synthesis as illustrated in FIG. 1A. The traditional solid phase matrix is a CPG bead with, for example, internal pores of 500 Å. To further evaluate the utility of solid phase initiator incorporation, CPG glass beads with SeqA-iBBr grown from the surface were suspended in a polymerization medium and a polymerization was conducted in situ using 5% monomer and 17000 ppm Cu (see (B) and (C) of FIG. 1B). After the reaction was completed, the beads were washed with water to remove any unreacted monomer and catalyst. The resulting beads were bright red in color, indicating polymer growth and incorporation of the rhodamine methacrylate monomer. The DNAPH was cleaved from the bead (see (D) in FIG. 1B) and analyzed using GPC, the results of which are illustrated in FIG. 9. Under the robust procedures hereof for formation of a polynucleotide-polymer hybrids such as DNAPH, grafting/blocking from reactions may be conducted either prior to, or after, the polynucleotide is removed from the solid support. In case in which the incorporated initiator functionality may not be stable under polynucleotide deprotection conditions (that is, base stable), the grafting-from polymerization may, for example, be conducted prior to deprotection. Certain RAFT initiator functionalities may, for example, not be stable under polynucleotide deprotection conditions.

In another embodiment hereof, the conjugated synthetic polymer segments include biocompatible monomer units which include additional stimuli responsive monomer units grown from this initiator using ATRP including incorporation of monomer units displaying, for example, photo, thermal, or pH responsive properties, as disclosed in incorporated references.

Using solid phase polynucleotide synthesis (for example, to prepare DNA, RNA, DNA/RNA, or derivatives thereof) and the methods hereof to prepare polynucleotide macroinitiators, one may prepare relatively large amounts of polynucleotide macroinitiators with high purity and in high yield. In a number of embodiments, the polynucleotide-initiator conjugates may, for example, be used to obtain block copolymers with hydrophilic synthetic copolymer segments exemplified herein by formation of a OEOMA and RMA using AGET and ARGET ATRP in the presence of biologically compatible low concentrations of catalyst. Polymerization conditions may be readily selected to provide polymer segments with well-defined molecular weights and narrow molecular weight distributions, using either a two-step approach in which the polynucleotide macroinitiator is isolated prior to growth of the polymer from the polynucleotide macroinitiator or in a one-step approach where the (co)polymer is grown from the polynucleotide macroinitiator while it is still attached to the solid support (thereby allowing a simple washing procedure to provide direct and rapid purification of the conjugates prior to separation from the solid support).

Figure 12:
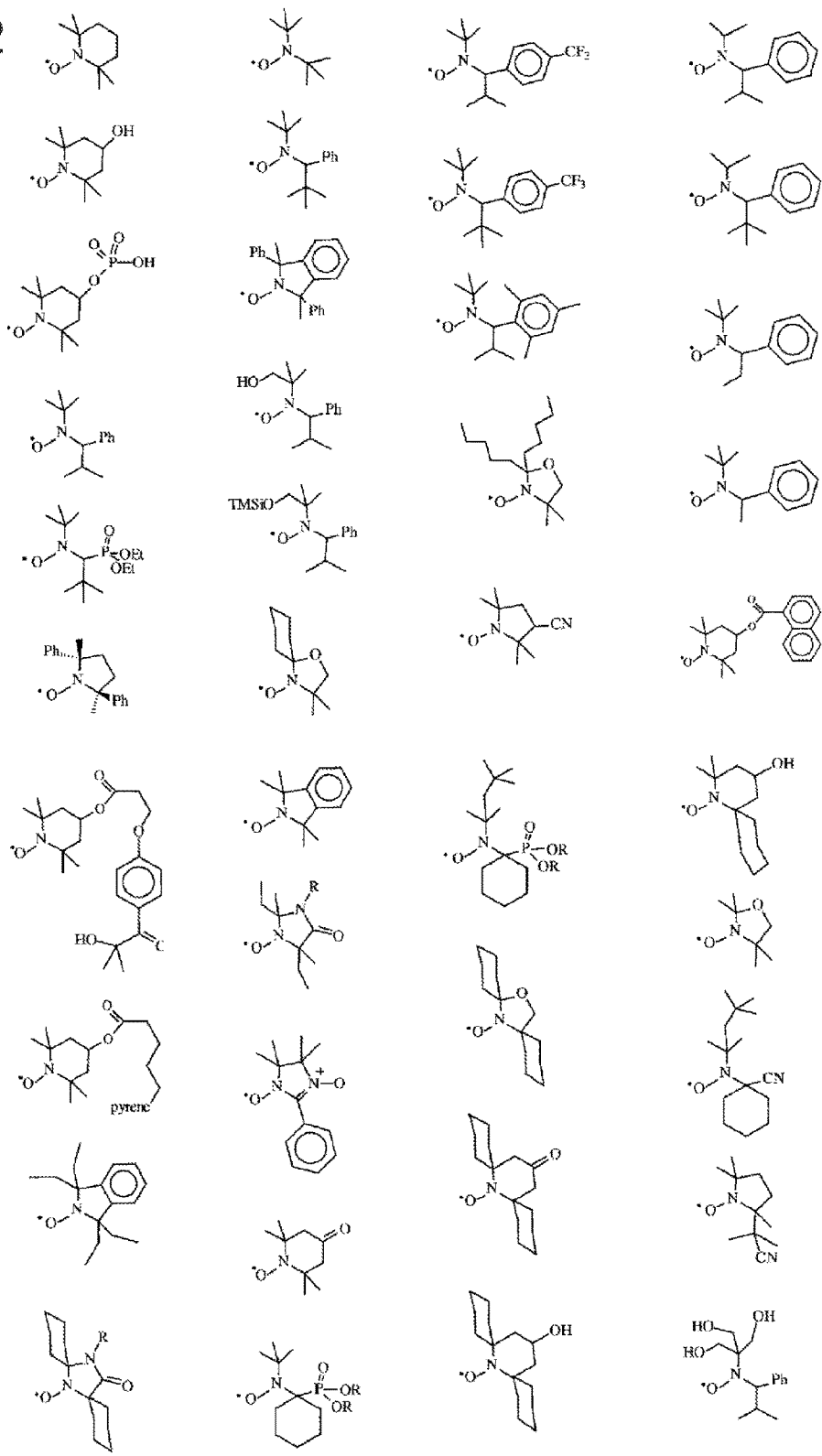
FIG. 12 illustrates example of nitroxides suitable for use in NMP.

The representative synthesis of an α,ω-difunctional DNA macroinitiator, Cy5-SeqA-iBBr, confirmed that the ATRP conditions did not damage the DNA sequence and, therefore, the developed polymerization methods may be readily applied to other polynucleotide sequences selected for developing functional DNAPHs as well as to other polynucleotide-polymer hybrids. The procedures hereof for grafting-from or blocking-from polynucleotides provide access to a wider variety of polynucleotide bioconjugates with higher yields and efficiency than previous polynucleotide bioconjugation methods. The procedures hereof provide efficient incorporation of a reversible deactivation radical polymerization initiator (for example, an ATRP, RAFT or NMP initiator) into a polynucleotide and the development of efficient blocking from conditions enables formation of bioconjugates under conditions that do not denature the covalently linked polynucleotide in any manner. The formed hybrid materials may, for example, find utility as functional biomaterials for drug delivery, imaging and as vaccines. Examples of nitroxides suitable as NMP initiators (for the nitroxyl groups hereof) are provided in FIG. 12. Suitable nitroxyl groups (nitroxides) are, for example, disclosed in Hawker, C. J. et al., New Polymer Synthesis by Nitroxide Mediated Living Radical Polymerizations, *Chem. Rev.*, 2001, 101, 3611-3688, Nicolas, J. et al., Nitroxide-mediated Polymerization, *Progress In Polymer Sci.*, 2013, 38, 63-235, and PCT International Patent Application Publication No. WO2007/078819, the disclosures of which are incorporated herein by reference. The first five nitroxyl groups (nitroxides) of the first column of FIG. 12 are commonly used.

As disclosed in PCT International Patent Application Publication No. WO2007/078819, in a number of embodiments, nitroxide free radicals may have the general structure:

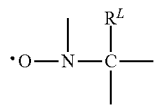

in which the monovalent $R^L$ radical has a molar mass greater than 15. The monovalent $R^L$ group is in the β-position with respect to the nitrogen atom of the nitroxide. The remaining valencies of the carbon atom and of the nitrogen atom of the nitroxide may be bonded to various groups, such as a hydrogen or a hydrocarbon group, for example a substituted or unsubstituted alkyl, aryl or aralkyl group comprising from 1 to 10 carbon atoms. The β-position may, for example, also be attached to a hydrogen. The carbon atom and the nitrogen atom may be connected via a bivalent group to form a ring. However, the remaining valencies of the carbon atom and of the nitrogen atom are preferably each bonded to monovalent groups. $R^L$ preferably has a molar mass greater than 30. $R^L$ may, for example, have a molar mass of between 40 and 450. $R^L$ may, for example, include a phosphoryl group, such as:

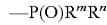

in which $R'''$ and $R''$ may, for example, be independently selected from alkyl, cycloalkyl, alkoxy, aryloxy, aryl, aralkyloxy, perfluoroalkyl and aralkyl groups and may include from 1-20 carbon atoms. $R'''$ and/or $R''$ may also be a halogen atom, such as a Cl or Br or F or I atom. $R^L$ may also include at least one aromatic ring, such as the phenyl radical or the naphthyl radical, which can be substituted, for example, with an alkyl group of 1-4 carbon atoms.

The stable free radical may, for example, be tert-butyl 1-phenyl-2-methylpropyl nitroxide, tert-butyl 1-(2-naphthyl)-2-methylpropyl nitroxide, tert-butyl 1-diethylphosphono-2,2-dimethylpropyl nitroxide, tert-butyl 1-dibenzylphosphono-2,2-dimethylpropyl nitroxide, phenyl 1-diethylphosphono-2,2-dimethylpropyl nitroxide, phenyl 1-diethylphosphono-1-methylethyl nitroxide, 1-phenyl-2-methylpropyl 1-diethylphosphono-1-methylethyl nitroxide. A commonly used stable free radical is N-t~butyl-N-[1-diethylphosphono-(2,2,-dimethylpropyl)]nitroxide (DEPN) which is illustrated as the fifth structure in the first column of FIG. 12.

In a number of embodiments, the robust methods hereof may be used to prepare DNABCp compatible with solid phase nucleic-acid synthesis strategies. Functionalized phosphoramidites including an initiator for reversible deactivation radical polymerization may be prepared using commonly available commercial reagents in, for example, a simple two-step procedure. Such procedures may, for example, be used for the preparation of chain end functionalized polymers utilizing a solid phase procedures wherein attached biomolecules can be directly conjugated to polymers and can be used to prepare screening quantities of functionalized bioactive materials.

The procedures hereof provide a direct method to prepare polynucleotides including initiator functionalities incorporated at known, preselected site(s) along the polynucleotide for the preparation of polynucleotide-polymer hybrids or conjugates with site specific grafted (co)polymer segments in the formed molecule. Compounds used to incorporate initiators (exemplified by functionalized phosphoramidite including a functional group suitable for initiating a "grafting from" polymerization) may, for example, additionally or alternatively include functionalities selected for tethering other bioresponsive molecules to the nucleic acid. In a number of embodiments, procedures hereof provide a direct method to prepare polynucleotides further including specific functionalities incorporated at known preselected site(s) along the nucleic acid for subsequent tethering of, for example, known bioactive molecules to the nucleic acid.

To further assess the compatibility of the methods hereof with a wide range of monomers and polymerization conditions, the functional iBBr-DNA1 was used in an AGET ATRP process to prepare hydrophobic polymers exemplified by using benzyl methacrylate (BnMA) and RMA. Because of its charged phosphate backbone and water solubility, iBBr-DNA1 can act as a reactive surfactant in dispersion polymerization to form DNA1-b-P(BnMA-co-RMA). The hydrophobicity of the polymer component results in aggregation of DNA1-b-P(BnMA-co-RMA) into large DNA-latex (DTEX) particles by dialysis of the DNA1-b-P(BnMA-co-RMA) into acetone and then into ultrapure water. The DTEX-DNA1 particles were characterized by dynamic light scattering and zeta potential analysis which showed well defined particles with a diameter of 1.3±0.09 μm and a zeta potential of negative 25.8±1 mV.

Figure 7B:
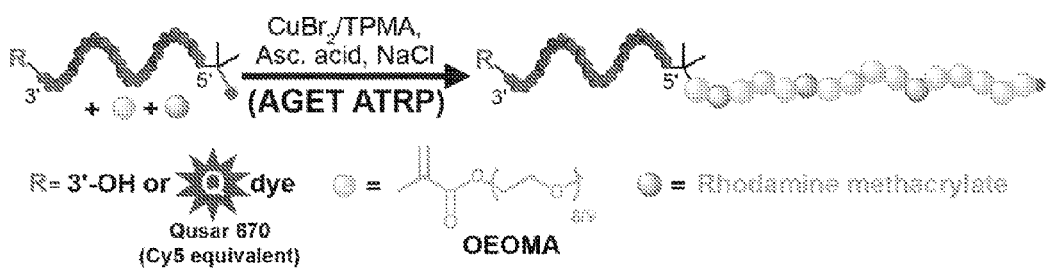
FIG. 7B illustrates schematically chain extension of a copolymer from Cy5-DNA-iBBr macroinitiator.
Figure 10A:
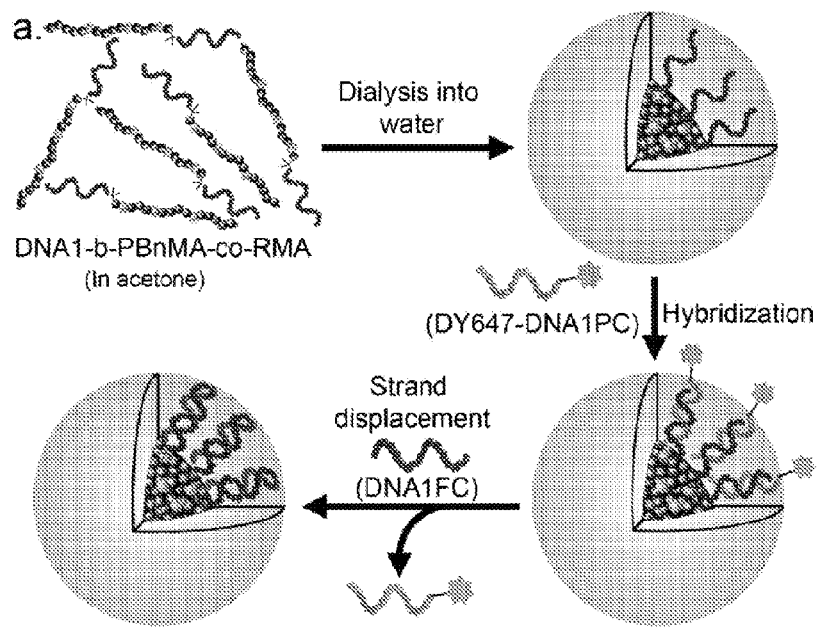
FIG. 10A illustrates synthesis of DNA-latex (DTEX) particles formed using a DNA1-b-PBnMA-co-RMA DNA-polymer hybrid.
Figure 10B:
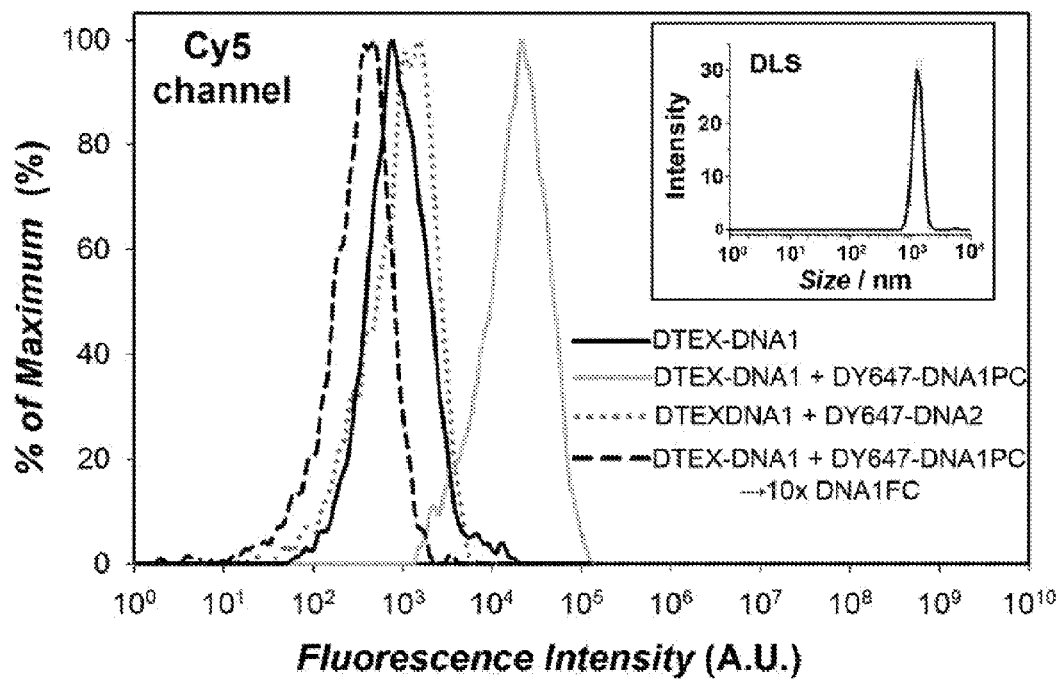
FIG. 10B illustrates the results of flow cytometry studied wherein detection in Cy5 channel reveals these sequence specific hybridizations, and wherein the inset illustrates the volume distribution of the DTEX particles by dynamic light scattering.

To test the integrity and sequence recognition properties of the DTEX particles imparted by the 23-mer DNA1, the particles were first annealed to a partially complementary DNA strand, DY647-DNA1PC that included a fluorescent dye (Dylight647, a Cy5 equivalent) and 18 matched nucleotides. FIGS. 10A and 10B summarizes the synthesis and characterization of DNA-latex (DTEX) particles. FIG. 10A illustrates the behavior of DNA1-b-PBnMA-co-RMA, obtained by block copolymerization from iBBr-DNA1 using BnMA and RMA monomers, during dialysis from acetone into water. The hydrophobic polymer chains aggregate to form the core of the particles. The outer surface of the DTEX particles, exposed to water, remains decorated with DNA1 that selectively binds DY647-DNA1PC (with fluorescent dye). This partially complementary strand could be displaced from the DTEX particles using strand DNA1FC that is fully complementary to the DNA1 sequence. FIG. 7B shows the flow cytometry with detection in Cy5 channel which reveals these sequence specific hybridzations. DTEX-DNA1 (black solid) shows a large increase in fluorescence when DY647-DNA1PC was hybridized (gray solid). When a non-complementary strand (DY647-DNA2) was used for hybridization, the Cy5 signal did not increase (gray dots). The DY647-DNA1PC hybridized to the DTEX-DNA1 could be completely displaced by fully complementary strand DNA1FC (with no fluorescent dye) and the Cy5 signal (black dashes) reverted to baseline levels. Inset shows the volume distribution of the DTEX particles by dynamic light scattering.

In FIG. 7B, the black solid trace shows a large increase in the fluorescence in the Cy5 channel when annealed to DY647-DNA1PC, gray solid trace. However, no such increase was observed when a non-complementary sequence Dy647-DNA2 (gray dots) was used, demonstrating the sequence specific recognition by DTEX-DNA1. Further, the partially complementary DY647-DNA1PC strand could be displaced from the particles with a 10× excess of DNA1FC that is fully complementary (all 23 residues) to the DTEX bound DNA1. As DNA1FC included no fluorescent dye, the signal in the Cy5 channel of DTEX-DNA1+DY647-DNA1PC after strand displacement with DNA1FC (black dashes) showed close correspondence to that of the initial DTEX-DNA1 and indicated complete displacement of the DY647-DNA1PC from the DTEX particles. The signal from the rhodamine channel for all particles that contain RMA in the hydrophobic polymer core remained unchanged suggesting stability of the polymer core. Overall, these experiments demonstrate that the DNA in these DNABCps retains the ability of sequence specific strand recognition following the synthesis of the polymer chain. The readily accessible DTEX particles, with their capacity for versatility in the polymer composition and DNA (or other polynucleotide) sequences, may, for example, be useful in biosensors and other applications.

The synthetic procedures hereof exemplify a broadly applicable approach for the direct preparation of well-defined bioconjugates from solid supports such as CPG beads and provide a general approach to the synthesis of biologically related molecule conjugated in polymer hybrids through solid phase incorporation of, for example, a phosphoramidite or other compound including a specific, stably linked initiator functionality.

In a number of representative embodiments, the procedures hereof may also, for example, be used in connection with the large variety and number of small molecule functionalized solid supports that are readily available, which will also allow rapid access to small (bio)molecule functionalized polymers. To demonstrate this concept, the representative ATRP initiator functionalized phosphoramidite described above was directly coupled with a biotin-CPG bead, and then a 'b-f' copolymerization of OEOMA and RMA was conducted from the solid support (that is, from beads functionalized with biotin; see FIG. 11A). Such a procedure may, for example, be carried out from any dye or any number of bioresponsive molecules, without necessarily having to first form a polynucleotide such as DNA and conjugate the desired functionality to the polynucleotide in a less efficient reaction.

After the AGET ATRP polymerization, the beads were washed and the biotin functionalized polymer was cleaved from the solid support using ammonium hydroxide. The biotin-polymer was characterized by GPC; the molar mass of the conjugate determined to be $M_n$=32 kDa with $M_w/M_n$=1.2.

To confirm that the biotin was intact at the chain end of the polymer, the polymer ability to bind to avidin microbeads (see FIG. 11B) was assessed using flow cytometry. The avidin microbeads themselves or the avidin microbeads with the OEOMA-RMA copolymer, without biotin showed little fluorescence in the flow cytometry experiment (see FIG. 11C, trace with maximum ~1-30 fluorescence units and trace with maximum ~40-100 fluorescence units). However, when the biotin terminated polymer was incubated with the avidin microbeads, a significant shift in the peak to higher fluorescence (FIG. 11C, trace centered at 250 fluorescence units) which indicates binding of the biotin polymer conjugate with the avidin microbeads.

The amidite-initiator conjugates hereof may, for example, be used to functionalize any hydroxyl-functional molecule present on a solid support or in solution in the manner described herein for the representative examples. A wide range of small-molecule functionalized solid supports (for example, CPG beads) are commercially available, incorporating, for example, many functional biologically relevant drugs, dyes or targeting agents. The procedures hereof permit ready and rapid functionalization of polymers with any of the diverse small molecules available for use in solid-phase synthesis of polynucleotides. As described above, this utility was exemplified by the synthesis of a biotin modified polymer on solid support using the an ATRP initiator functionalized phosphoramidite, thereby confirming that the procedures hereof can also be employed to incorporate unique α-functionality into the initiator utilizing solid phase synthesis and conducting a grafting from the initiator prior to removal of the novel α-functionalized bioconjugate from the CPG and deprotection.

EXPERIMENTAL

Commercially available compounds were used without further purification unless otherwise noted. CuBr$_2$ (98%), and N,N,N',N",N"-pentamethyldiethylenetriamine (PMDETA, 98%) were purchased from Aldrich (Saint Louis, Mo.). CuBr (98%, Acros Organics of Morris Plains, N.J.) was purified by stirring in acetic acid, filtered, washed with 2-propanol and then dried under vacuum. Oligo(ethylene oxide) monomethyl ether methacrylate (average molecular weight ~300, OEOMA) and ethylene glycol diacrylate (EGDA, 90%) were purchased from Aldrich and purified by passing through a column filled with basic alumina to remove the inhibitor and/or antioxidant. Copper sulfate pentahydrate (CuSO$_4$.5H$_2$O) was purchased from Sigma Aldrich. HPLC grade acetonitrile (ACN) was purchased from Fisher Scientific (Hampton, N.H.). Sodium ascorbate was purchased from Alfa Aesar (Ward Hill, Mass.), α-Bromoisobutyryl bromide, 4-amino-1-butanol, Oligo(ethylene oxide) monomethyl ether methacrylate (average molecular mass ~475 g/mol, OEOMA), diphenyl ether, ascorbic acid, CuBr$_2$, NH$_4$OH and 3-Hydroxypicolinic acid (3-HPA, MALDI matrix) were from Sigma Aldrich in the highest available purity. RhodamineB methacrylate (RMA) was purchased from Polysciences, Inc. (Warrington, Pa.). Tris (2-pyridylmethyl)amine (TPMA) was purchased from ATRP Solutions. Diisopropylethylamine (DIPEA), triethylyamine (Et$_3$N), 1-methyl-imidazole and organic solvents for reaction and chromatography were purchased from VWR. Avidin coated polystyrene particles were obtained from Spherotech (Lake Forest, Ill.). SPECTRA/POR® 7 dialysis tubing (25 k MWCO) was purchased from Spectrum Laboratories Inc. (Compton, Calif.). Standard DNA phosphoramidites with ultramild protecting groups (dA-PAC, dC-PAC and dG-$^t$Bu-PAC) and the 2-cyanoethyl-N,N-diisopropyl-chloro-phosphoramidite were purchased from Chemgenes (Wilmington, Mass., USA). Appropriate reagents for solid phase DNA synthesis (deblock, activator, ultramild CapA, CapB and oxidation reagent) were purchased from Glen Research (Sterling, Va., USA). CPG solid supports for DNA synthesis (both dC and Quasar670) were purchased from Biosearch Technologies (Novato, Calif., USA). Monomers were passed over a column of basic alumina prior to use. Other solvents and reagents not otherwise specified were purchased from Fisher. The 5'-phosphohexynyl modifier and DYLIGHT™ 547 phosphoramidites were purchased from Glen Research. CPG columns for 3'-O-propargyl DNA were purchased from ChemGenes.

Molecular weight and polydispersity were measured by GPC (PSS Polymer Standards Services of Mainz, Fed Rep Germany) columns (guard, 105, 103, and 102 Å), with THF eluent at 35° C., flow rate 1.00 mL/min, and differential refractive index (RI) detector (Waters, 2410 refractive index detector available from Waters Corporation of Milford, Mass.). Toluene was used as the internal standard to correct for any fluctuation of the THF flow rate. The apparent molecular weights and polydispersity were determined with a calibration based on linear polystyrene standards using WINGPC® 6.0 GPC software from PSS Polymer Standards Service. The detectors employed to measure the absolute molecular weights (Mw,MALLS) were a triple detector system containing RI detector (Wyatt Technology of Santa Barbara, Calif., OPTILAB® REX), viscometer detector (Wyatt Technology, VISCOSTAR™) and a multi-angle laser light scattering (MALLS) detector (Wyatt Technology, DAWN® EOS™) with the light wavelength at 690 nm. Absolute molecular weights were determined using ASTRA® software from Wyatt Technology. DNAs were synthesized as described below Infrared spectra (IR) were obtained on a JASCO® FTIR 6300 instrument available from Jasco Inc. of Easton, Md. UV-vis spectra were obtained on a NANODROP® 1000 spectrophotometer available from NanoDrop Technologies of Wilmington, Del. Emission spectra were obtained on a NanoDrop 3300.

Example 1

Synthesis of Phosphoramidite Containing an ATRP Initiating Functionality

As illustrated in FIGS. 2,4-Amino-1-butanol (5 g, 0.0561 mol) and triethylamine (6.24 g, 0.0624 mol) were dissolved in 20 ml of dichloromethane and α-bromoisobutyryl bromide (12.8 g, 0.0567 mol) was added drop wise. The reaction was stirred for 16 hours. The reaction mixture was filtered and stirred with 20 ml of 5% KOH for 2 hours. The reaction mixture was then added to a separatory funnel and the aqueous layer was separated. The organic layer was then washed with 1N NaOH (25 ml 2×), 1N HCl (25 ml 2×) brine (25 ml 1×) dried over $MgSO_4$ filtered and the solvent was evaporated. $^1H$ NMR (300 MHz, $CDCl_3$): 7.0 ppm (s 1H) 3.7 ppm (t 2H) 3.3 ppm (t 2H), 2.2 ppm (s 1H), 1.9 ppm (s 6H), 1.6 ppm (m 4H).

DIPEA (1.24 mL, 7.14 mmol), 2-cyanoethoxy-N, N-diisopropyl chlorophosphine (478 μL, 2.14 mmol) and 1-methyl-imidazole (57 μL, 0.713 mmol) were added to a solution of alcohol (340 mg, 1.43 mmol) in $CH_2Cl_2$ (10 mL). The mixture was stirred for 30 mins at 0° C. and 1.5 hour at room temperature. Work up was done with $NaHCO_3$ (saturated)/EtOAc. Column chromatography (EtOAc/Hexane, 1:1) gives the product (515 mg) in 82% isolated yield. $^1H$ NMR (300 MHz, $CDCl_3$): δ 1.15 (d, J=2.6 Hz, 6H), 1.17 (d, J=2.6 Hz, 6H), 1.60-1.69 (m, 4H), 1.93 (s, 6H), 2.63 (app t, J=6.44 Hz, 2H), 3.26-3.32 (m, 2H), 3.52-3.91 (m, 6H), 6.77 (s, 1H); $^{13}C$ NMR (75 MHz, $CDCl_3$): δ 20.2, 20.3, 24.4, 24.5, 24.5, 24.6, 25.9, 28.3, 28.4, 32.4, 39.9, 42.8, 43.0, 58.0, 58.3, 62.9, 63.0, 63.1, 117.5, 171.8; $^{31}P$ NMR (127 MHz, $CDCl_3$): 147.65; Mass (ESI): m/z=439 [M$^+$+H], 461 [M$^+$+Na].

Example 2

Synthesis of Free Standing DNA Macroinitiators

Solid phase oligonucleotide synthesis was performed on a MerMade 4 instrument (available from Bioautomation of Plano, Tex.). Synthesis of the oligonucleotides was conducted on commercially available solid support columns and performed with standard commercially available phosphoramidites as directed by the manufacturer. Cleavage off the solid support and base deprotection of the oligonucleotides was performed by exposing the beads to ammonium hydroxide at 65° C. for 2 h under standard protocols for PAC protected amidites as recommended by the manufacturer. Desalting and purification was conducted using C18 columns (Waters) using protocols recommended by the manufacturer, with elution of the full length desired DNAs with ACN and water.

An exemplary DNA comprising an ATRP initiator will be identified in the following text as DNA SeqA-IBBr.

Example 3

Blocking from DNA Macroinitiators

Recently developed conditions for AGET ATRP in aqueous media were employed as a starting point. The concentration of the SeqA-iBBr macroinitiator was set at 1 mM and the feed rate of the reducing agent, via syringe pump, was set to 500 nL/min of a 5 mM solution of ascorbic acid. The variables in the reaction were: sodium chloride concentration, the addition of salt to the reaction enhances deactivation which leads to better control over the polymerization, which was varied from 50-300 mM. The concentration of the catalysts species, copper$^{II}$bromide:TPMA (1:8), which was varied from ~9000 ppm to ~45000 ppm (by mole to monomer). The targeted degrees of polymerization were varied from ~100 to ~500 and the total reaction times were varied from 0.5 hrs to 2 hours. The conditions and results are summarized in Table 1 above.

Prior to characterizing the formed SeqA-b-(POEOMA-co-RMA) block copolymers the reaction mixtures were dried and dissolved in dimethylformamide, with 0.5% diphenyl ether as internal standard, and injected into a DMF GPC with poly(ethylene oxide) calibration. When characterizing the grafted polymer for chain-end functionality using fluorescence spectroscopy the reactions were purified using dialysis with a 25 k MWCO membrane into ultrapure water.

Several key factors were found to influence control over the block copolymer growth. These are a relatively low salt concentration, 50 mM, and a copper$^{II}$bromide:TPMA concentration of at least 22000 ppm, Using these conditions polymers with molecular weights close to theoretical molecular weights and low molecular weight distributions (MWD<1.2) are readily obtainable at various targeted degrees of polymerization.

Entry 9 in Table 1 reports conditions employed for chain extension with a hydrophobic monomer, benzyl methacrylate, and RMA.

Example 4

Incorporation of α-Functionality into a DNA Macroinitiator

To prove that the SeqA-iBBr macro initiator was not degraded during the preparation of the DNAPH an α-functionalized DNA macro-initiator was prepared, Cy5-SeqA-iBBr, and the optimized conditions from the previous studies were employed for a blocking from this α,ω-difunctional DNA. After extensive purification of the reaction mixture using dialysis a FRET analysis was conducted. The Cy5 excitation was due to the RMA copolymer donor emission (control experiments showed that neither simply adding Cy5 to a SeqA-b-POEOMA-co-RMA nor direct excitation of Cy5 at 520 nm leads to the emission observed), FIG. 3. This indicates that the DNA did not degrade during polymerization. Conditions employed for the polymerization reaction shown in the second stage of the reaction shown in FIG. 1 employed the following ratio of reagents $[OEOMA_{475}]_0$:$[FITCMA]_0$:$[dA13\text{-}iBBr]_0$:$[CuBr_2]_0$:$[TPMA]_0$=4220:25:1:22:180, in a reaction conducted at room temperature in 50 mM NaCl, with ascorbic acid added to the reaction at a rate of 0.5 nmol/min.

Example 5

Conditions Used to Graft a Copolymer from Cy5-DNA-iBBr

The ratio of reagents: M/Rh-MA/I/TPMA/CuBr$_2$=496/2/1/4.2/34.3 (17000 ppm Cu) and 50 nM NaCl. The ascorbic acid reducing agent, (FRAA) was added to the reaction mixture at a rate of 5 nmol/min to continuously form a low concentration of the CuBr/TPMA activator complex. The polymerization was allowed to progress for 60 min. providing a conjugate with I+$M_{n\ th} \times 10^{-3}$=250 and $M_{n\ GPC} \times 10^{-3}$=305 with $M_w/M_n$=1.15. The reaction product was purified using dialysis (25 k MWCO Spectrapore 7 filter into 1×PBS). The sample was concentrated using lipholization prior to conducting FRET analysis. Furthermore, polymer conjugation to the DNA was further confirmed using the control experiment where Cy5 was simply mixed with a DNA-block-POEOMA-co-Rhodamine and minimal FRET transfer was observed, at equimolar concentrations.

Example 6

Formation of an In Situ DNA Block Copolymer Conjugate (See FIG. 1B)

Direct polymerization from a CPG bead using the AGET ATRP conditions developed for solution phase DNAPH block copolymer synthesis would be convenient in terms of purification of the final product. This was accomplished by suspending 2.5 mg of CPG beads with SeqA-iBBr immobilized on their surface in a polymerization medium comprising 5% monomer and 17000 ppm CuBr$_2$/TPMA (1:8). The polymerization was conducted in situ and activated by slow feeding of an ascorbic acid solution into the suspension to generate the active catalyst species. After the reaction the beads were extensity washed to remove any unreacted monomer and catalyst. The beads were bright red in color indicating polymer growth and incorporation of the rhodamine methacrylate monomer. The DNAPH was cleaved from the bead, using ammonium hydroxide, and lyophilized. The polymer was analyzed using DMF GPC, which showed that a polymer with a molecular weight of 2.05 kDa and an $M_w/M_n$ of 1.43, FIG. 6.

Example 7

Figure 11A:
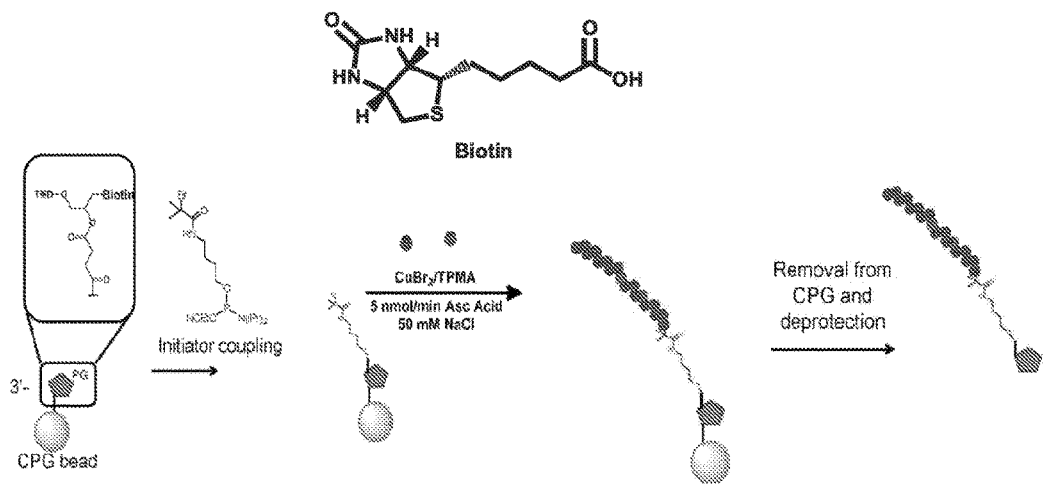
FIG. 11A illustrates schematically a procedure employed for incorporation of an α-functionalized initiator utilizing solid phase synthesis and grafting from the incorporated initiator prior to removal of the conjugate from the CPG and deprotection.

Grafting from Modified Biotin on Solid Support (See FIG. 11A)

5.6 mg of CPG beads with Biotin-iBBr, 14 mg of OEOMA, 20 μL of the RMA stock solution (at 10 mg/ml), 10 μL of the catalyst stock solution (at 10 mg/ml), 55 μL of ultrapure water and 4.4 μL of 1M NaCl were combined in a two necked 2 ml pear shaped flask equipped with a small magnetic stirrer. The reaction was degassed by passing a stream of nitrogen gas over the stirring reaction mixture for 20 min. A degassed ascorbic acid solution was then slow feed into the reaction mixture at a rate of 0.5 μL/min. The reaction was carried out for 1.5 hours. The beads were extensively washed and the Biotin-POEOMA-co-RMA was cleaved with ammonium hydroxide and lyophilized.

Example 8

Figure 11B:
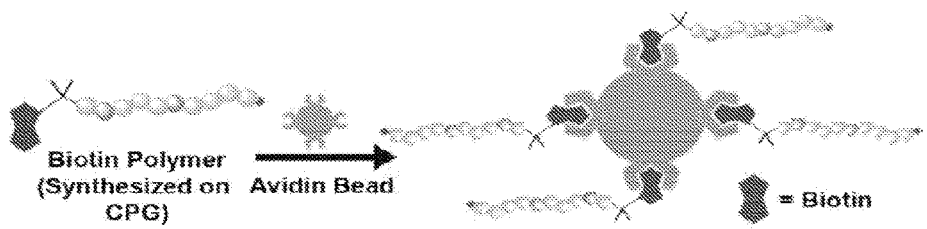
FIG. 11B illustrates schematically an avidin binding assay performed to characterize the biotin conjugated polymer using flow cytometry.
Figure 11C:
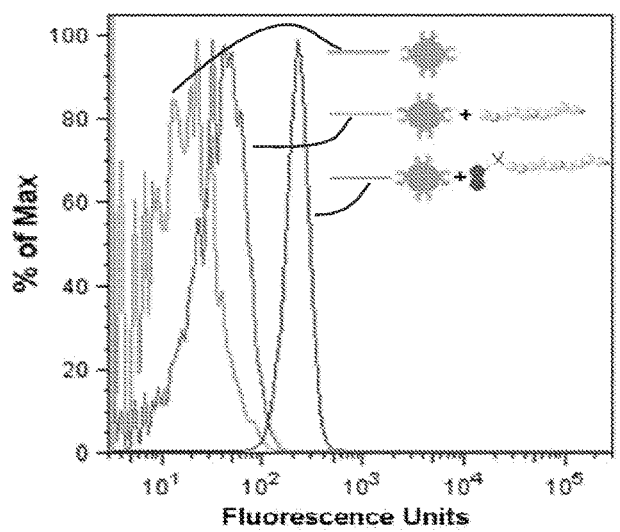
FIG. 11C illustrates results of FRET analysis of the biotin conjugated polymer.

Biotin-block-POEOMA-co-RhMA Avadin Microbead Binding (See FIG. 11B)

The Biotin-POEOMA-co-RMA and a control sample (of POEOMA-co-RMA (no biotin)) were dissolved in 1×PBS buffer at a concentration of 1 mg/ml. Biotin-POEOMA-co-RMA (200 μL) or a control of POEOMA-co-RMA (no biotin) control (200 μL) were mixed with 20 μL of Streptavadin polystyrene beads (5.1 μM), respectively. The mixture was subjected to 5 min of centrifugation at 2000 rpm and resuspended in 1 ml of ultra-pure water and analyzed using flow cytometry; 10000 beads were counted per run. The avidin microbeads themselves or the avidin microbeads with the OEOMA-RMA copolymer (without biotin) showed little fluorescence in the flow cytometry experiment. However, when the biotin terminated polymer was incubated with the avidin microbeads, a significant shift in the peak to higher fluorescence indicates binding of the biotin polymer conjugate with the avidin microbeads, See FIG. 11C. In this manner the biotin was shown to be present on the present on the formed hybrid copolymer by binding to the surface of an avidin labeled microbead.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of synthesizing a polynucleotide composition comprising: attaching a compound comprising at least one initiator or at least one transfer agent for a reversible deactivation radical polymerization to an end of a nucleotide chain assembly immobilized upon a solid phase support during a solid phase synthesis of a polynucleotide so that the initiator or the transfer agent is attached to the end of a nucleotide chain assembly in a manner which is stable under conditions of deprotection of the polynucleotide, and growing a polymer from the initiator or from a site of the chain transfer agent via the reversible deactivation radical polymerization to form the polynucleotide composition.

2. The method of claim 1 wherein the initiator or the chain transfer agent is attached to the end of a nucleotide chain assembly in a manner which is stable under conditions of detachment of the polynucleotide from the solid phase support.

3. The method of claim 2 wherein the polymer is grown from the polynucleotide while the polynucleotide is attached to the solid phase support or after the polynucleotide is detached from the solid phase support.

4. The method of claim 3 wherein the polynucleotide is a ribonucleic acid (RNA), a deoxyribonucleic acid (DNA), a DNA/RNA hybrid, or a derivative thereof.

5. The method of claim 3 wherein the compound is attached to the nucleotide chain assembly at an intermediate position within the polynucleotide or at the terminus of the polynucleotide.

6. The method of claim 3 wherein the compound comprising the initiator or the transfer agent has the formula $R^1$-L-$(R^2—)_n$—$R^3$, wherein $R^1$ comprises a group adapted to react with the end of the nucleotide chain assembly, L is a base stable spacer group, wherein $R^2$ is a base stable linking group, wherein n is 0 or an integer in the range of 1 to 20, and $R^3$ is a residue of an initiator or a residue of a chain transfer agent for a reversible deactivation radical polymerization.

7. The method of claim 6 wherein L is selected from the group consisting of

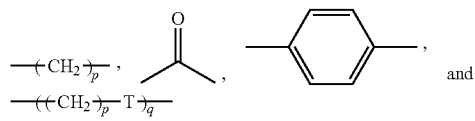

and wherein T is selected from the group O, S, —C(O)NH— or —NHC(O)—, p is an integer between 1 and 18 and q is an integer between 1 and 18.

8. The method of claim 7 wherein $R^2$ is selected from the group consisting of

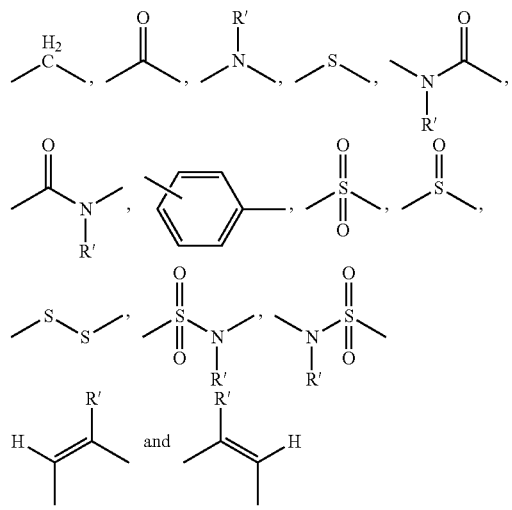

wherein R' is selected from the group of H, alkyl and aryl.

9. The method of claim 8 wherein $R^1$ comprises a phosphoramidite group, an azide group, an alkyne group, an N-hydroxysuccinimide ester group, a maleimide group, a dibromomaleimide group or a thiol group.

10. The method of claim 8 wherein $R^1$ comprises a phosphoramidite group.

11. The method of claim 10 wherein the phosphoramidite group has the formula

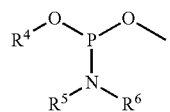

wherein $R^4$ is $(CH_2)_rCN$, wherein r is an integer in the range of 1-5, and $R^5$ and $R^6$ are each independently selected from the group consisting of methyl, ethyl, propyl, pentyl, hexyl or heptyl.

12. The method of claim 10 wherein $R^3$ has the formula:

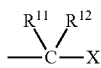

wherein X is a homolytically cleavable group or a group activated by degenerative radical exchange;

$R^{11}$, $R^{12}$ are each independently selected from the group consisting of a homolytically cleavable group, a group activated by degenerative radical exchange, H, $C_1$-$C_{20}$ alkyl, $C_3$-$C_8$ cycloalkyl, $C(=Y)R^{15}$, $C(=Y)NR^{16}R^{17}$, COCl, OH, CN, $C_2$-$C_{20}$ alkenyl, $C_2$-$C_{20}$ alkynyl, oxiranyl, glycidyl, aryl, heterocyclyl, aralkyl, aralkenyl, $C_1$-$C_6$ alkyl in which from 1 to all of the hydrogen atoms are replaced with halogen and $C_1$-$C_6$ alkyl substituted with from 1 to 3 substituents selected from the group consisting of $C_1$-$C_4$ alkoxy, aryl, heterocyclyl, $C(=Y)R^{15}$, $C(=Y)NR^{16}R^{17}$, oxiranyl and glycidyl, wherein $R^{15}$ is $C_1$-$C_{20}$ alkyl, $C_1$-$C_{20}$ alkoxy, aryloxy or heterocyclyloxy, and $R^{16}$ and $R^{17}$ are independently H, or $C_1$-$C_{20}$ alkyl, or $R^{16}$ and $R^{17}$ may be joined together to form an alkylene group of from 2 to 5 carbon atoms, wherein Y is $NR^{18}$ or O and $R^{18}$ is H, straight or branched $C_1$-$C_{20}$ alkyl or aryl.

13. The method of claim 12 wherein X is selected from the group consisting of Cl, Br, I, nitroxyl, organotellurium, organostibine, organobismuthine, and —S—C(=S)—Z, wherein Z is selected from the group consisting of alkyl, alkoxy, alkylthio, aryl, and heteroaryl.

14. The method of claim 3 wherein the initiator of the transfer agent is bound to a phosphoramidite via the base stable linking group which is selected from the group consisting of

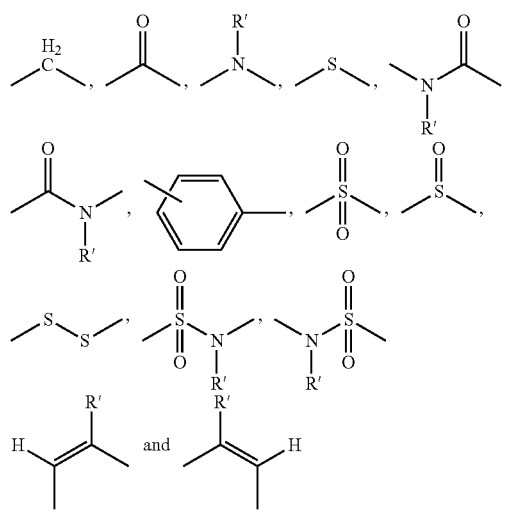

wherein where R' is selected from the group consisting of H, alkyl and aryl, and the phosphoramidite is reacted with a free hydroxyl group of the end of the nucleotide chain assembly.

15. The method of claim 3 further comprising removal of the polynucleotide from the solid support and deprotection of the polynucleotide.

16. The method of claim 1 wherein the polymer is grown from the initiator or from the site of the transfer agent under aqueous conditions or in the presence of a polar solvent and the polymer is hydrophilic or water soluble, or the polymer is grown from the initiator or from the site of the transfer agent under non-aqueous conditions and the polymer is hydrophobic or water insoluble.

17. The method of claim 4 wherein the compound is attached at a 2'-position, a 5'-position or a 3'-position.

18. The method of claim 1 wherein the at least one initiator or the at least one transfer agent participates in an ATRP reaction, a RAFT reaction, a concurrent ATRP/RAFT reaction or a NMP reaction.

19. The method of claim 18 wherein the initiator for ATRP is adapted to initiate a controlled ATRP in the presence of a catalyst complex formed with an excess of ligand under polymerization conditions wherein the polynucleotide is stable.

20. A composition having the formula $R^1$-L-($R^2$—)$_n$—$R^3$, wherein $R^1$ is a phosphoramidite, L is a base stable spacer group, wherein $R^2$ is a base stable linking group, wherein n is 0 or an integer in the range of 1 to 20, and $R^3$ is a residue of an initiator or a chain transfer agent for a reversible deactivation radical polymerization.

21. The composition of claim 20 wherein L is selected from the group consisting of

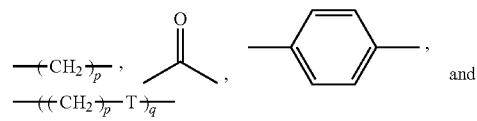

wherein T is selected from the group O, S, —C(O)NH— or —NHC(O)—, p is an integer between 1 and 18 and q is an integer between 1 and 18.

22. The composition of claim 20 wherein $R^2$ is selected from the group consisting of

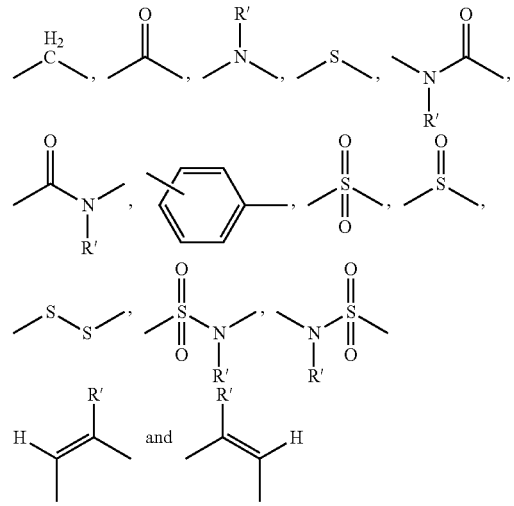

wherein where R' is selected from the group consisting of H, alkyl and aryl.

23. A method of forming a composition for growth of a polymer via reversible deactivation radical polymerization therefrom, comprising: attaching at least one initiator or at least one transfer agent for a reversible deactivation radical polymerization to a first compound by reacting a second compound with the first compound, the second compound having the formula $R^1$-L-$(R^2-)_n$—$R^3$, wherein $R^1$ is a phosphoramidite, L is a base stable spacer group, $R^2$ is a base stable linking group, wherein n is 0 or an integer in the range of 1 to 20, and $R^3$ is a residue of an initiator or a residue of a transfer agent for a reversible deactivation radical polymerization.

\* \* \* \* \*

SEQUENCE LISTING

<160> NUMBER OF SEQ ID NOS: 1

<210> SEQ ID NO 1
<211> LENGTH: 23
<212> TYPE: DNA
<213> ORGANISM: Artificial Sequence
<220> FEATURE:
<223> OTHER INFORMATION: The sequences was designed with complementary
      base-pairs that enable detection, labeling and analysis of the
      strands.

<400> SEQUENCE: 1
gcactgcagt tggatcccat agc                                              23